United States Patent
Wham et al.

(10) Patent No.: US 12,333,423 B2
(45) Date of Patent: Jun. 17, 2025

(54) SYSTEMS AND METHODS FOR ESTIMATING TISSUE PARAMETERS USING SURGICAL DEVICES

(71) Applicant: Covidien LP, Mansfield, MA (US)

(72) Inventors: Robert H. Wham, Boulder, CO (US); Jing Zhao, Superior, CO (US)

(73) Assignee: Covidien LP, Mansfield, MA (US)

( * ) Notice: Subject to any disclaimer, the term of this patent is extended or adjusted under 35 U.S.C. 154(b) by 938 days.

(21) Appl. No.: 16/777,266

(22) Filed: Jan. 30, 2020

(65) Prior Publication Data

US 2020/0265309 A1 Aug. 20, 2020

Related U.S. Application Data

(60) Provisional application No. 62/805,596, filed on Feb. 14, 2019, provisional application No. 62/805,583, filed on Feb. 14, 2019.

(51) Int. Cl.
*G06N 3/08* (2023.01)
*A61B 17/00* (2006.01)
(Continued)

(52) U.S. Cl.
CPC ....... *G06N 3/08* (2013.01); *A61B 17/320092* (2013.01); *A61B 18/1445* (2013.01);
(Continued)

(58) Field of Classification Search
CPC .. G06N 3/08; G16H 10/40; A61B 17/320074; A61B 18/1445;
(Continued)

(56) References Cited

U.S. PATENT DOCUMENTS

| D574,323 S | 8/2008 | Waaler |
| 7,720,267 B2 | 5/2010 | Fuchs et al. |

(Continued)

FOREIGN PATENT DOCUMENTS

| DE | 179607 C | 11/1906 |
| DE | 390937 C | 3/1924 |

(Continued)

OTHER PUBLICATIONS

Vallfors et al., "Automatically Controlled Bipolar Electrosoagulation—'COA-COMP'", Neurosurgical Review 7:2-3 (1984) pp. 187-190.

(Continued)

*Primary Examiner* — Linda C Dvorak
*Assistant Examiner* — Abigail Bock

(57) ABSTRACT

A computer implemented method for estimating tissue parameters, includes collecting data, from a surgical system including an instrument and an energy source, the data including at least one electrical parameter associated with delivering energy from the instrument to tissue, communicating the data to at least one machine learning algorithm, determining, using the at least one machine learning algorithm, a tissue parameter based upon the data, communicating the determined tissue parameter to a computing device associated with the energy source for use in formulating an energy-delivery algorithm for delivering energy from the instrument to tissue, and delivering energy from the instrument of the surgical system to tissue in accordance with the energy-delivery algorithm.

20 Claims, 12 Drawing Sheets

(51) Int. Cl.
*A61B 17/32* (2006.01)
*A61B 18/00* (2006.01)
*A61B 18/12* (2006.01)
*A61B 18/14* (2006.01)
*A61B 18/18* (2006.01)
*G06N 3/049* (2023.01)
*G06Q 50/06* (2024.01)
*G16H 10/40* (2018.01)

(52) U.S. Cl.
CPC ......... *A61B 18/1815* (2013.01); *G06N 3/049* (2013.01); *G16H 10/40* (2018.01); *A61B 2017/00199* (2013.01); *A61B 2017/0023* (2013.01); *A61B 2017/00734* (2013.01); *A61B 2017/00973* (2013.01); *A61B 2017/320074* (2017.08); *A61B 2018/00577* (2013.01); *A61B 2018/0063* (2013.01); *A61B 2018/00779* (2013.01); *A61B 2018/00827* (2013.01); *A61B 2018/00845* (2013.01); *A61B 2018/00892* (2013.01); *A61B 2018/1253* (2013.01); *A61B 2018/126* (2013.01); *G06Q 50/06* (2013.01)

(58) Field of Classification Search
CPC ...... A61B 18/1815; A61B 2018/00577; A61B 2018/00779; A61B 2018/00827; A61B 2018/00845; A61B 2018/00892; G06Q 50/06
See application file for complete search history.

(56) References Cited

U.S. PATENT DOCUMENTS

| | | | |
|---|---|---|---|
| 8,831,327 | B2 | 9/2014 | Santamaria-Pang et al. |
| 9,099,863 | B2 | 8/2015 | Smith et al. |
| 9,186,202 | B2 | 11/2015 | Gilbert |
| 9,270,202 | B2 | 2/2016 | Johnson et al. |
| 9,283,028 | B2 | 3/2016 | Johnson |
| 2004/0167508 | A1 | 8/2004 | Wham et al. |
| 2006/0036372 | A1 | 2/2006 | Yener et al. |
| 2009/0187177 | A1* | 7/2009 | Epstein ................. A61B 18/16 606/35 |
| 2009/0298703 | A1 | 12/2009 | Gough et al. |
| 2014/0232463 | A1 | 8/2014 | Gilbert |
| 2014/0243815 | A1 | 8/2014 | Kerr |
| 2014/0253140 | A1 | 9/2014 | Gilbert |
| 2014/0257270 | A1 | 9/2014 | Behnke |
| 2014/0258800 | A1 | 9/2014 | Gilbert |
| 2014/0276750 | A1 | 9/2014 | Gilbert |
| 2014/0276753 | A1 | 9/2014 | Wham et al. |
| 2014/0276754 | A1 | 9/2014 | Gilbert et al. |
| 2014/0358138 | A1 | 12/2014 | Mattmiller et al. |
| 2014/0376269 | A1 | 12/2014 | Johnson et al. |
| 2015/0025521 | A1 | 1/2015 | Friedrichs et al. |
| 2015/0025523 | A1 | 1/2015 | Friedrichs et al. |
| 2015/0032096 | A1 | 1/2015 | Johnson |
| 2015/0032098 | A1 | 1/2015 | Larson et al. |
| 2015/0032099 | A1 | 1/2015 | Larson et al. |
| 2015/0032100 | A1 | 1/2015 | Coulson et al. |
| 2015/0088116 | A1 | 3/2015 | Wham |
| 2015/0088117 | A1 | 3/2015 | Gilbert et al. |
| 2015/0088118 | A1 | 3/2015 | Gilbert et al. |
| 2015/0088124 | A1 | 3/2015 | Wham |
| 2015/0088125 | A1 | 3/2015 | Wham |
| 2015/0119871 | A1 | 4/2015 | Johnson et al. |
| 2015/0320481 | A1* | 11/2015 | Cosman, Jr. ........... A61B 34/10 606/35 |
| 2018/0125575 | A1* | 5/2018 | Schwartz ............. G16H 10/60 |
| 2018/0235686 | A1* | 8/2018 | Sahakian ............. A61B 18/148 |
| 2019/0200998 | A1* | 7/2019 | Shelton, IV ......... A61B 5/0066 |
| 2020/0022649 | A1* | 1/2020 | Rodriguez ........... A61B 5/4878 |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 102008058737 A1 | 4/2010 |
| EP | 0246350 A1 | 11/1987 |
| EP | 0267403 A2 | 5/1988 |
| EP | 0296777 A2 | 12/1988 |
| EP | 0310431 A2 | 4/1989 |
| EP | 0325456 A2 | 7/1989 |
| EP | 0336742 A2 | 10/1989 |
| EP | 0390937 A1 | 10/1990 |
| EP | 0556705 A1 | 8/1993 |
| EP | 0608609 A2 | 8/1994 |
| EP | 0836868 A2 | 4/1998 |
| EP | 0880220 A2 | 11/1998 |
| EP | 0882955 A1 | 12/1998 |
| EP | 1051948 A2 | 11/2000 |
| EP | 1366724 A1 | 12/2003 |
| EP | 1776929 A1 | 4/2007 |
| FR | 1275415 A | 11/1961 |
| FR | 1347865 A | 1/1964 |
| FR | 2313708 A1 | 12/1976 |
| FR | 2364461 A1 | 4/1978 |
| FR | 2502935 A1 | 10/1982 |
| FR | 2517953 A1 | 6/1983 |
| FR | 2573301 A1 | 5/1986 |
| JP | 63005876 | 1/1988 |
| JP | 2002065690 A | 3/2002 |
| JP | 2005185657 A | 7/2005 |
| SU | 166452 | 11/1964 |
| SU | 727201 A2 | 4/1980 |
| WO | 0211634 A1 | 2/2002 |
| WO | 0245589 A2 | 6/2002 |
| WO | 03090635 A1 | 11/2003 |
| WO | 2006050888 A1 | 5/2006 |
| WO | 2008053532 A1 | 5/2008 |
| WO | 2014140085 A1 | 9/2014 |

OTHER PUBLICATIONS

Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Richard Wolf Medical Instruments Corp. Brochure, "Kleppinger Bipolar Forceps & Bipolar Generator", 3 pp. Jan. 1989.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Cosman et al., "Radiofrequency Lesion Generation and Its Effect on Tissue Impedance", Applied Neurophysiology 51: (1988) pp. 230-242.

(56) References Cited

OTHER PUBLICATIONS

Goldberg et al., "Tissue Ablation with Radiofrequency: Effect of Probe Size, Gauge, Duration, and Temperature on Lesion Volume" Acad Radio (1995) vol. 2, No. 5, pp. 399-404.
U.S. Appl. No. 10/406,690 dated Apr. 3, 2003 inventor: Behnke.
U.S. Appl. No. 10/573,713 dated Mar. 28, 2006 inventor: Wham.
U.S. Appl. No. 11/242,458 dated Oct. 3, 2005 inventor: Becker.

* cited by examiner

SYSTEMS AND METHODS FOR ESTIMATING TISSUE PARAMETERS USING SURGICAL DEVICES

CROSS-REFERENCE TO RELATED APPLICATIONS

This application claims the benefit of U.S. Provisional Patent Application Nos. 62/805,596 and 62/805,583, both filed on Feb. 14, 2019, the entire contents of each of which are hereby incorporated herein by reference.

FIELD

The disclosure relates to estimating tissue parameters and, more particularly, to systems and methods incorporating machine learning-based estimation of tissue parameters to control surgical devices based on the estimated tissue parameters.

BACKGROUND

Surgical instruments are utilized to perform various functions on tissue structures. A surgical forceps, for example, is a plier-like device which relies on mechanical action between its jaws to grasp, clamp, and constrict tissue. Energy-based surgical forceps utilize both mechanical clamping action and energy to treat, e.g., coagulate, cauterize, and/or seal, tissue.

Surgical instruments such as energy-based surgical forceps are effective at treating tissue, tissue treatment is typically effected without tissue temperature feedback. For example, with respect to energy-based surgical forceps, vessel sealing is accomplished by subjecting a vessel to a specific energy profile under a specific pressure.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

In accordance with aspects of the disclosure, a computer implemented method for estimating tissue parameters is presented. The computer implemented method includes collecting data, from a surgical system including an instrument and an energy source, the data including at least one electrical parameter associated with delivering energy from the instrument to tissue, communicating the data to at least one machine learning algorithm, determining, using the at least one machine learning algorithm, a tissue parameter based upon the data, communicating the determined tissue parameter to a computing device associated with the energy source for use in formulating an energy-delivery algorithm for delivering energy from the instrument to tissue, and delivering energy from the instrument of the surgical system to tissue in accordance with the energy-delivery algorithm.

In an aspect of the disclosure, the method further includes measuring data from the electrosurgical system, wherein the data includes at least one of a voltage, a current, or a frequency.

In another aspect of the disclosure, the at least one machine learning algorithm includes a neural network.

In an aspect of the disclosure, the neural network includes at least one of a temporal convolutional network or a feed forward network.

In yet another aspect of the disclosure, communicating the data to at least one machine learning algorithm includes shifting data into the machine learning algorithm one time step at a time, and determining the tissue parameter includes estimating, by the machine learning algorithm, the tissue parameter one time step at a time.

In a further aspect of the disclosure, the method further includes training the neural network using one or more of observing sensor data or identifying patterns in data.

In a further aspect of the disclosure, the method further includes training the neural network using training data including at least one of: impedance, power, time, tissue electrical properties, tissue thermal properties, electrical properties of the instrument, thermal properties of the instrument, size of the instrument, shape of the instrument, frequency, voltage, current, balun temperature, or transformer temperature.

In another aspect of the disclosure, the determining the tissue parameter includes determining at least one of tissue temperature, tissue mass, tissue surface area, steam formation/release, collagen denaturing, tissue pressure, collagen/gelatin flow, tissue size/mass changes, or tissue water content.

In a further aspect of the disclosure, the energy source is adapted to generate energy for treating tissue, the energy source including one or more output terminals which supply energy to the tissue, the one or more output terminals operatively connected to one or more supply lines, the energy source including one or more return terminals configured to return energy from the tissue, the return terminals being operatively connected to one or more return lines, wherein the surgical system further includes a cable housing a portion of the one or more supply lines and the one or more return lines, and wherein the instrument is operatively connected to the cable.

In another aspect in accordance with the disclosure, the surgical system includes at least one of a microwave ablation system, an electrosurgical system, or an ultrasonic surgical instrument.

In accordance with aspects of the disclosure, a system for estimating tissue parameters is presented. The system includes an electrosurgical system, a processor(s), and at least one memory coupled to the one or more processors, the at least one memory having instructions stored thereon which, when executed by the one or more processors, cause the system to collect data, from a surgical system including an instrument and an energy source, the data including at least one electrical parameter associated with delivering energy from the instrument to tissue, communicate the data to at least one machine learning algorithm, determine, using the at least one machine learning algorithm, a tissue parameter based on the data, communicate the determined tissue parameter to a computing device associated with the energy source for use in formulating an energy-delivery algorithm for delivering energy from the instrument to tissue, and delivering energy from the instrument of the surgical system to tissue in accordance with the energy-delivery algorithm.

In yet a further aspect of the disclosure, the instructions, wherein collecting the data from the surgical system includes measuring at least one of a voltage, a current, a power, or a frequency.

In yet another aspect of the disclosure, the at least one machine learning algorithm includes a neural network. In a further aspect of the present disclosure, the neural network includes a temporal convolutional network and/or a feed forward network. In yet a further aspect of the present disclosure, the instructions, when executed by the one or more processors, further cause the system to shift data one time step at a time, and predict, by the machine learning algorithm, the tissue temperature at a next step.

In another aspect of the disclosure, communicating the data to at least one machine learning algorithm includes: shifting data into the machine learning algorithm one time step at a time, and determining the tissue parameter includes estimating, by the machine learning algorithm, the tissue parameter one time step at a time.

In a further aspect of the disclosure, the instructions, when executed by the one or more processors, further cause the system to train the neural network using one or more of observing sensor data or identifying patterns in data. In an aspect of the present disclosure, the instructions, when executed by the one or more processors, further cause the system to train the neural network using training data including at least one of: impedance, power, time, tissue electrical properties, tissue thermal properties, electrical properties of the instrument, thermal properties of the instrument, size of the instrument, shape of the instrument, frequency, voltage, current, balun temperature, or transformer temperature.

In a further aspect of the disclosure, the determining includes determining tissue temperature without a temperature sensor.

In another aspect of the disclosure, the energy source is adapted to generate energy for treating tissue, the energy source including one or more output terminals which supply energy to the tissue, the one or more output terminals operatively connected to one or more supply lines, the energy source including one or more return terminals configured to return energy from the tissue, the return terminals being operatively connected to one or more return lines. The surgical system further includes a cable housing a portion of the one or more supply lines and the one or more return lines. The instrument is operatively connected to the cable.

In another aspect of the disclosure, the surgical system includes at least one of a microwave ablation system, an electrosurgical system, or an ultrasonic surgical instrument.

In accordance with aspects of the disclosure, a computer implemented method for estimating tissue parameters is presented. The computer implemented method includes collecting data, from an electrosurgical system, the data including a time, a power, or an impedance, communicating the data to at least one machine learning algorithm, determining a tissue temperature based on an output of a machine learning algorithm, communicating the determined tissue temperature to a computing device for use in formulating a tissue sealing algorithm, and supplying electrosurgical energy from the electrosurgical system to tissue in accordance with the tissue sealing algorithm.

In an aspect of the disclosure, the method further includes measuring data from the electrosurgical system, wherein the data includes at least one of a voltage or a current. The at least one of the voltage and the current are used to derive at least one of the power or the impedance.

In another aspect of the disclosure, the at least one machine learning algorithm includes a neural network.

In an aspect of the disclosure, the neural network includes at least one of a temporal convolutional network layer or a feed forward network layer.

In yet another aspect of the disclosure, the method further includes shifting data one time step at a time, and predicting, by the machine learning algorithm, the tissue temperature at a next step.

In a further aspect of the disclosure, the method further includes training the neural network using one or more of observing sensor data or identifying patterns in data.

In an aspect of the disclosure, the method further includes training the neural network using identifying patterns in an impedance shape and a power.

In a further aspect of the disclosure, the method further includes training the neural network using training data including at least one of: impedance, power, time, tissue electrical properties, tissue thermal properties, electrosurgical device electrical properties, or electrosurgical device thermal properties.

In yet another aspect of the disclosure, method further includes predicting, by the machine learning algorithm at least one of tissue temperature, tissue mass, tissue surface area, steam formation/release, collagen denaturing, tissue pressure, collagen/gelatin flow, tissue size/mass changes, or tissue water content.

In a further aspect of the disclosure, the electrosurgical system includes a generator adapted to generate electrosurgical energy for treating tissue, the generator including one or more output terminals which supply energy to the tissue, the one or more output terminals operatively connected to one or more supply lines, the generator also including one or more return terminals configured to return energy from the tissue, the return terminals being operatively connected to one or more return lines, an electrosurgical cable housing a portion of the one or more supply lines and the one or more return lines, and an electrosurgical instrument operatively connected to the electrosurgical cable.

In accordance with aspects of the disclosure, a system for estimating tissue parameters is presented. The system includes an electrosurgical system, a processor(s), and at least one memory coupled to the one or more processors, the at least one memory having instructions stored thereon which, when executed by the one or more processors, cause the system to collect data, from an electrosurgical system, the data including at least one of a time, a power, or an impedance, communicate the data to at least one machine learning algorithm, determine a tissue temperature based on an output of the at least one machine learning algorithm, communicate the determined tissue temperature to a computing device for use in formulating a tissue sealing algorithm, and supplying electrosurgical energy from the electrosurgical system to tissue in accordance with the tissue sealing algorithm.

In yet a further aspect of the disclosure, the instructions, when executed by the one or more processors, further cause the system to measure data from the electrosurgical system, wherein the data includes at least one of a voltage or a current. The voltage and/or the current are used to derive the power or the impedance.

In yet another aspect of the disclosure, the at least one machine learning algorithm includes a neural network. In a further aspect of the present disclosure, the neural network includes a temporal convolutional network and/or a feed forward network. In yet a further aspect of the present disclosure, the instructions, when executed by the one or more processors, further cause the system to shift data one time step at a time, and predict, by the machine learning algorithm, the tissue temperature at a next step.

In yet another aspect of the disclosure, the instructions, when executed by the one or more processors, further cause the system to train the neural network using one or more of observing sensor data or identifying patterns in data.

In a further aspect of the disclosure, the instructions, when executed by the one or more processors, further cause the system to train the neural network using identifying patterns in an impedance shape and a power. In an aspect of the present disclosure, the instructions, when executed by the one or more processors, further cause the system to train the neural network using training data including at least one of: impedance, power, time, tissue electrical properties, tissue thermal properties, electrosurgical device electrical properties, or electrosurgical device thermal properties.

In another aspect of the disclosure, the instructions, when executed by the one or more processors, further cause the system to predict, by the machine learning algorithm at least one of tissue temperature, tissue mass, tissue surface area, steam formation/release, collagen denaturing, tissue pressure, collagen/gelatin flow, tissue size/mass changes, or tissue water content In a further aspect of the disclosure, the electrosurgical system includes a generator adapted to generate electrosurgical energy for treating tissue, the generator including one or more output terminals which supply energy to the tissue, the one or more output terminals operatively connected to one or more supply lines, the generator also including one or more return terminals configured to return energy from the tissue, the return terminals being operatively connected to one or more return lines, an electrosurgical cable housing a portion of the one or more supply lines and the one or more return lines, and an electrosurgical instrument operatively connected to the electrosurgical cable.

BRIEF DESCRIPTION OF THE DRAWINGS

Various aspects and features of the disclosure are described herein with reference to the drawings wherein.

DETAILED DESCRIPTION

Tissue sealing involves heating tissue to liquefy the collagen and elastin in the tissue so that it reforms into a fused mass with significantly-reduced demarcation between the opposing tissue structures. To achieve a tissue seal without causing unwanted damage to tissue at the surgical site or collateral damage to adjacent tissue, it is necessary to control the application of energy to tissue, thereby controlling the temperature of tissue during the sealing process. To properly seal tissue, a balance must be sustained during the sealing process between sufficient heating to denature proteins and vaporize fluids and poor seal performance.

With respect to utilizing tissue temperature information in real-time in order to control the application of energy to tissue to achieve a tissue seal, it would be desirable to determine tissue temperature during the tissue sealing process without the need for temperature sensors built into the jaw members of an electrosurgical instrument, as such temperature sensors increase costs and complexity. As detailed below, this may be accomplished by utilizing data already available from the electrosurgical system and running a machine learning algorithm to estimate tissue temperature based upon that data. The estimated tissue temperature may then be fed back to the controller for use in controlling the application of energy to tissue in accordance therewith.

The systems and methods of the disclosure detailed below may be incorporated into any type of surgical system for treating tissue such as, for example, the electrosurgical systems detailed hereinbelow. For purposes of illustration and in no way limiting the scope of the appended claims, the systems and methods for estimating tissue temperature for use in controlling application of energy to tissue are described in the disclosure in the context of electrosurgical systems.

Figure 1A:
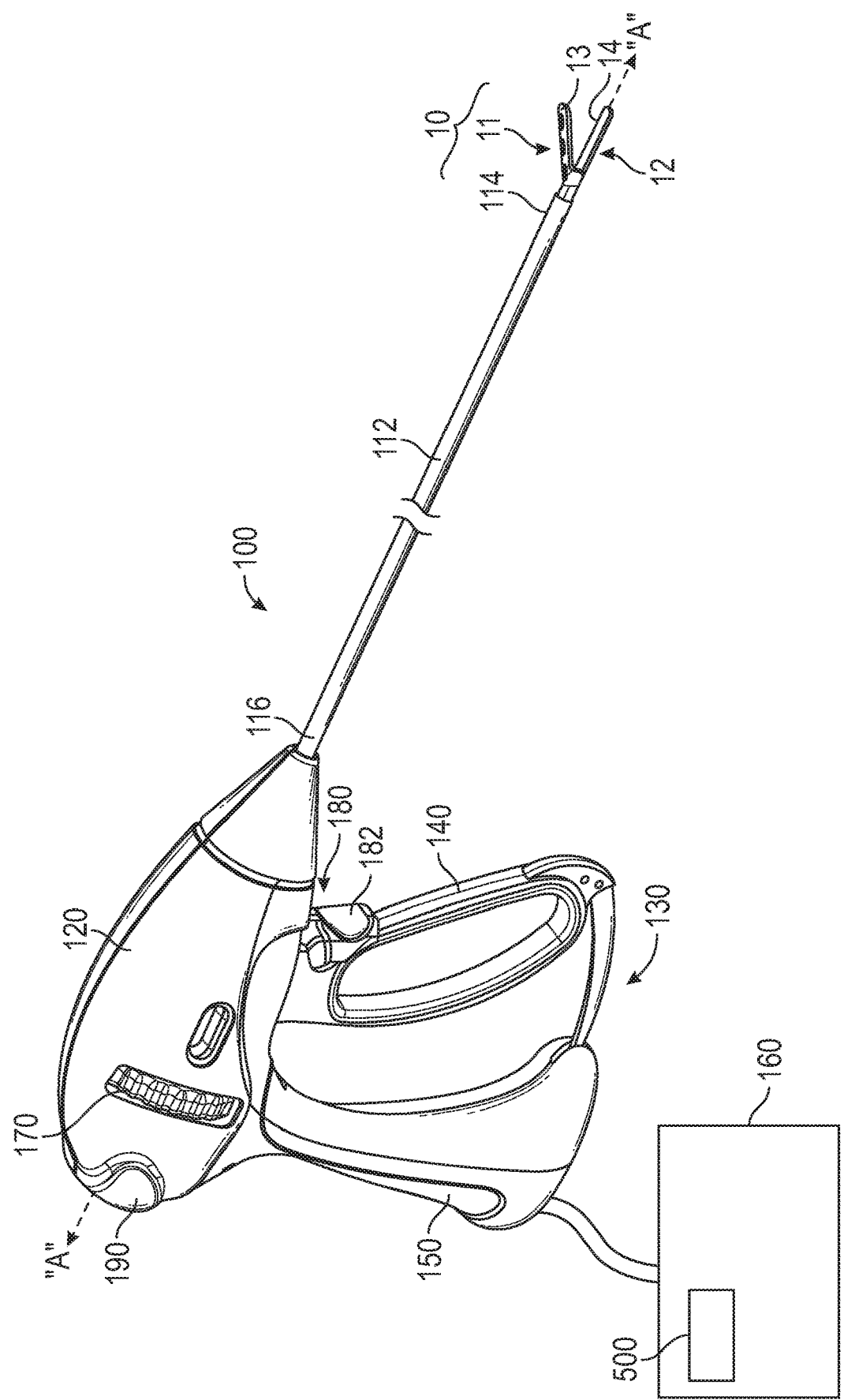
FIG. 1A is a perspective view of a surgical system provided in accordance with the disclosure including an energy-based surgical instrument and a generator.
Figure 1B:
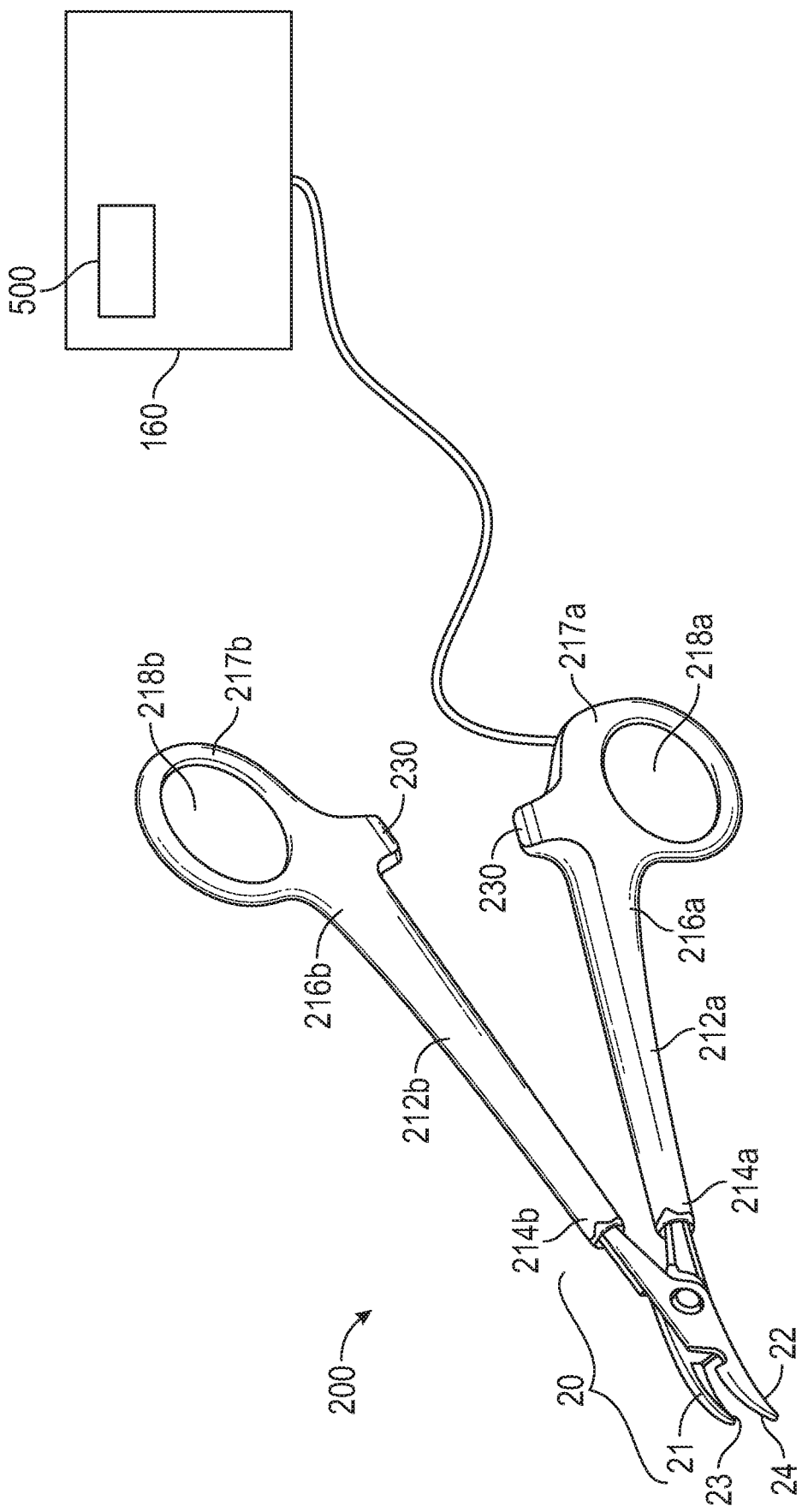
FIG. 1B is a perspective view of another surgical system provided in accordance with the present disclosure including another energy-based surgical instrument and the generator.

Referring now to FIGS. 1A and 1B, FIG. 1A depicts an electrosurgical system including an endoscopic surgical forceps 100 for use in connection with endoscopic surgical procedures and an electrosurgical generator 160 for use therewith, and FIG. 1B depicts an electrosurgical system including an open surgical forceps 200 contemplated for use in connection with traditional open surgical procedures and electrosurgical generator 160 for use therewith. For the purposes herein, either endoscopic forceps 100, open forceps 200, or any other suitable surgical instrument and/or system may be utilized in accordance with the disclosure.

Obviously, different electrical and mechanical connections and considerations apply to each particular type of instrument and system; however, the aspects and features of the disclosure remain generally consistent regardless of the configuration of the instrument or system used therewith.

Turning now to FIG. 1A, endoscopic forceps 100 defines a longitudinal axis "A-A" and includes a housing 120, a handle assembly 130, a rotating assembly 170, a trigger assembly 180 and an end effector assembly 10. Forceps 100 further includes a shaft 112 having a distal end 114 configured to mechanically engage end effector assembly 10 and a proximal end 116 that mechanically engages housing 120. Forceps 100 may further include a surgical cable extending therefrom and configured to connect forceps 100 to an electrosurgical generator 160 such that at least one of the electrically-conductive tissue treating surfaces 13, 14 of jaw members 11, 12 of end effector assembly 10 may be energized to treat tissue grasped therebetween, e.g., upon activation of activation switch 190.

With continued reference to FIG. 1A, handle assembly 130 includes fixed handle 150 and a movable handle 140. Fixed handle 150 is integrally associated with housing 120 and handle 140 is movable relative to fixed handle 150. Rotating assembly 170 is rotatable in either direction about a longitudinal axis "A-A" to rotate end effector assembly 10 about longitudinal axis "A-A." Housing 120 houses the internal working components of forceps 100.

End effector assembly 10 is shown attached at distal end 114 of shaft 112 and includes a pair of opposing jaw members 11 and 12. Each of jaw members 11 and 12 includes an electrically-conductive tissue treating surface 13, 14, respectively, configured to grasp tissue therebetween and conduct electrosurgical energy therethrough to treat, e.g., seal, tissue. End effector assembly 10 is designed as a unilateral assembly, i.e., where jaw member 12 is fixed relative to shaft 112 and jaw member 11 is movable relative to shaft 112 and fixed jaw member 12. However, end effector assembly 10 may alternatively be configured as a bilateral assembly, i.e., where both jaw member 11 and jaw member 12 are movable relative to one another and to shaft 112. In some embodiments, a knife assembly (not shown) is disposed within shaft 112 and a knife channel (not shown) is defined within one or both jaw members 11, 12 to permit reciprocation of a knife blade (not shown) therethrough, e.g., upon activation of trigger 182 of trigger assembly 180.

Continuing with reference to FIG. 1A, movable handle 140 of handle assembly 130 is ultimately connected to a drive assembly (not shown) that, together, mechanically cooperate to impart movement of jaw members 11 and 12 between a spaced-apart position and an approximated position to grasp tissue between tissue treating surfaces 13 and 14 of jaw members 11, 12, respectively. As shown in FIG. 1A, movable handle 140 is initially spaced-apart from fixed handle 150 and, correspondingly, jaw members 11, 12 are in the spaced-apart position. Movable handle 140 is depressible from this initial position to a depressed position corresponding to the approximated position of jaw members 11, 12.

Referring now to FIG. 1B, open forceps 200 is shown including two elongated shafts 212a and 212b, each having a proximal end 216a and 216b, and a distal end 214a and 214b, respectively. Forceps 200 is configured for use with an end effector assembly 20 that is similar to end effector assembly 10 of forceps 100 (see FIG. 1A). More specifically, end effector assembly 20 is attached to distal ends 214a and 214b of shafts 212a and 212b, respectively and includes a pair of opposing jaw members 21 and 22 that are movable relative to one another. Each shaft 212a and 212b includes a handle 217a and 217b disposed at the proximal end 216a and 216b thereof. Each handle 217a and 217b defines a finger hole 218a and 218b therethrough for receiving a finger of the user. As can be appreciated, finger holes 218a and 218b facilitate movement of shafts 212a and 212b relative to one another from an open position, wherein jaw members 21 and 22 are disposed in spaced-apart relation relative to one another, to a closed position, wherein jaw members 21 and 22 cooperate to grasp tissue therebetween.

A ratchet 230 may be included for selectively locking jaw members 21 and 22 of forceps 200 relative to one another at various different positions. It is envisioned that ratchet 230 may include graduations or other visual markings that enable the user to easily and quickly ascertain and control the amount of closure force desired between the jaw members 21 and 22.

With continued reference to FIG. 1B, one of the shafts may be adapted to receive a surgical cable configured to connect forceps 200 to a power source (not shown). Alternatively, forceps 200 may be configured as a battery powered instrument having an internal or integrated power source (not shown). The power source (not shown), as will be described in greater detail below, provides power to end effector assembly 20 such that at least one of the electrically-conductive tissue treating surfaces 23, 24 of jaw members 21, 22, respectively, of end effector assembly 20 may be energized to treat tissue grasped therebetween.

Similar to forceps 100 (FIG. 1A), forceps 200 may further include a knife assembly (not shown) disposed within either of shafts 212a, 212b and a knife channel (not shown) defined within one or both jaw members 21, 22 to permit reciprocation of a knife blade (not shown) therethrough.

Figure 1C:
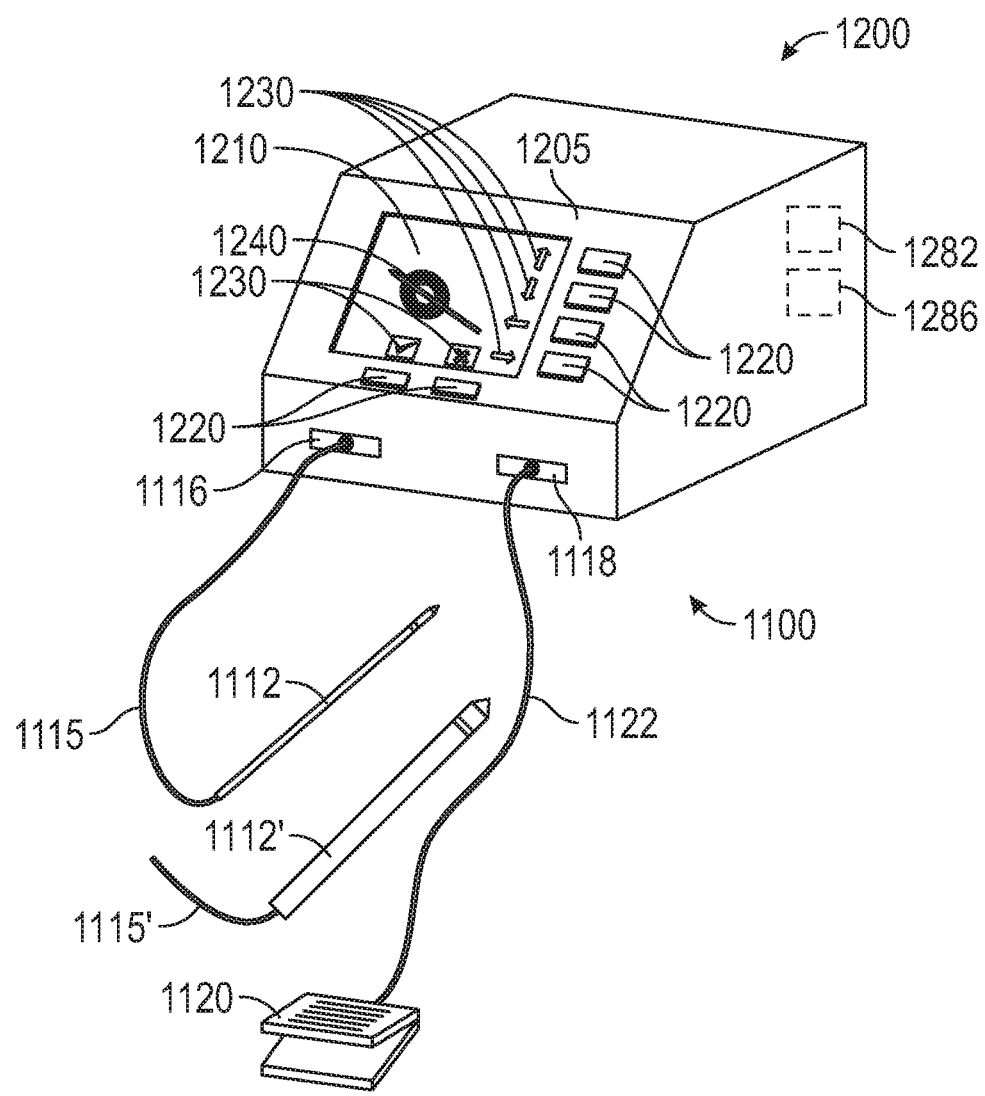
FIG. 1C is a perspective view of a microwave ablation system that includes a generator having a user interface for displaying and controlling ablation patterns in accordance with the disclosure.

Referring now to FIG. 1C, illustrated is a microwave ablation system 1100 in accordance with the present disclosure. The system 1100 includes a generator 1200, microwave antenna probe 1112 operably coupled by a cable 1115 via connector 1116 to the generator 1200, and an actuator 1120, which may be a footswitch, a handswitch, a bite-activated switch, or any other suitable actuator. Actuator 1120 is operably coupled by a cable 1122 via connector 1118 to generator 1200. Cable 1122 may include one or more electrical conductors for conveying an actuation signal from actuator 1120 to generator 1200. In embodiments, actuator 1120 is operably coupled to generator 1200 by a wireless link, such as without limitation, a radiofrequency or infrared link.

At least one additional or alternative microwave antenna probe 1112' may be included with microwave ablation system 1100 that may have characteristics distinct from that of microwave antenna probe 1112. For example without limitation, microwave antenna probe 1112 may be a 12 gauge probe suitable for use with energy of about 915 MHz, while microwave antenna probe 1112' may be a 14 gauge probe suitable for use with energy of about 915 MHz. Other probe variations are contemplated within the scope of the present disclosure, for example without limitation, a 12 gauge operable at 2450 MHz, and a 14 gauge operable at 2450 MHz. In use, the surgeon may interact with user interface 1205 of generator 1200 to preview operational characteristics of available probes 1112, 1112' and to choose a probe for use.

Generator 1200 includes a generator module 1286 that is configured as a source of microwave energy and is disposed in operable communication with processor 1282. In embodiments, generator module 1286 is configured to provide energy of about 915 MHz. Generator module 1286 may also be configured to provide energy of about 2450 MHz (2.45 GHz.). The present disclosure contemplates embodiments wherein generator module 1286 is configure to generate a frequency other than about 915 MHz or about 2450 MHz, and embodiments wherein generator module 1286 is configured to generate variable frequency energy. Probe 1112 is operably coupled to an energy output of generator module 1286.

Generator assembly 1200 also includes user interface 1205, that may include a display 1210 such as, without limitation, a flat panel graphic LCD display, adapted to visually display at least one user interface element 1230, 1240. In embodiments, display 1210 includes touchscreen capability (not explicitly shown), e.g., the ability to receive input from an object in physical contact with the display, such as without limitation a stylus or a user's fingertip, as will be familiar to the skilled practitioner. A user interface element 1230, 1240 may have a corresponding active region, such that, by touching the screen within the active region associated with the user interface element, an input associated with the user interface element is received by the user interface 1205.

User interface 1205 may additionally or alternatively include one or more controls 1220, that may include without limitation a switch (e.g., pushbutton switch, toggle switch, slide switch) and/or a continuous actuator (e.g., rotary or linear potentiometer, rotary or linear encoder.) In embodiments, a control 1220 has a dedicated function, e.g., display contrast, power on/off, and the like. Control 1220 may also have a function which may vary in accordance with an operational mode of the ablation system 1100. A user interface element 1230 may be positioned substantially adjacently to control 1220 to indicate the function thereof. Control 1220 may also include an indicator, such as an illuminated indicator (e.g., a single- or variably-colored LED indicator).

Figure 1D:
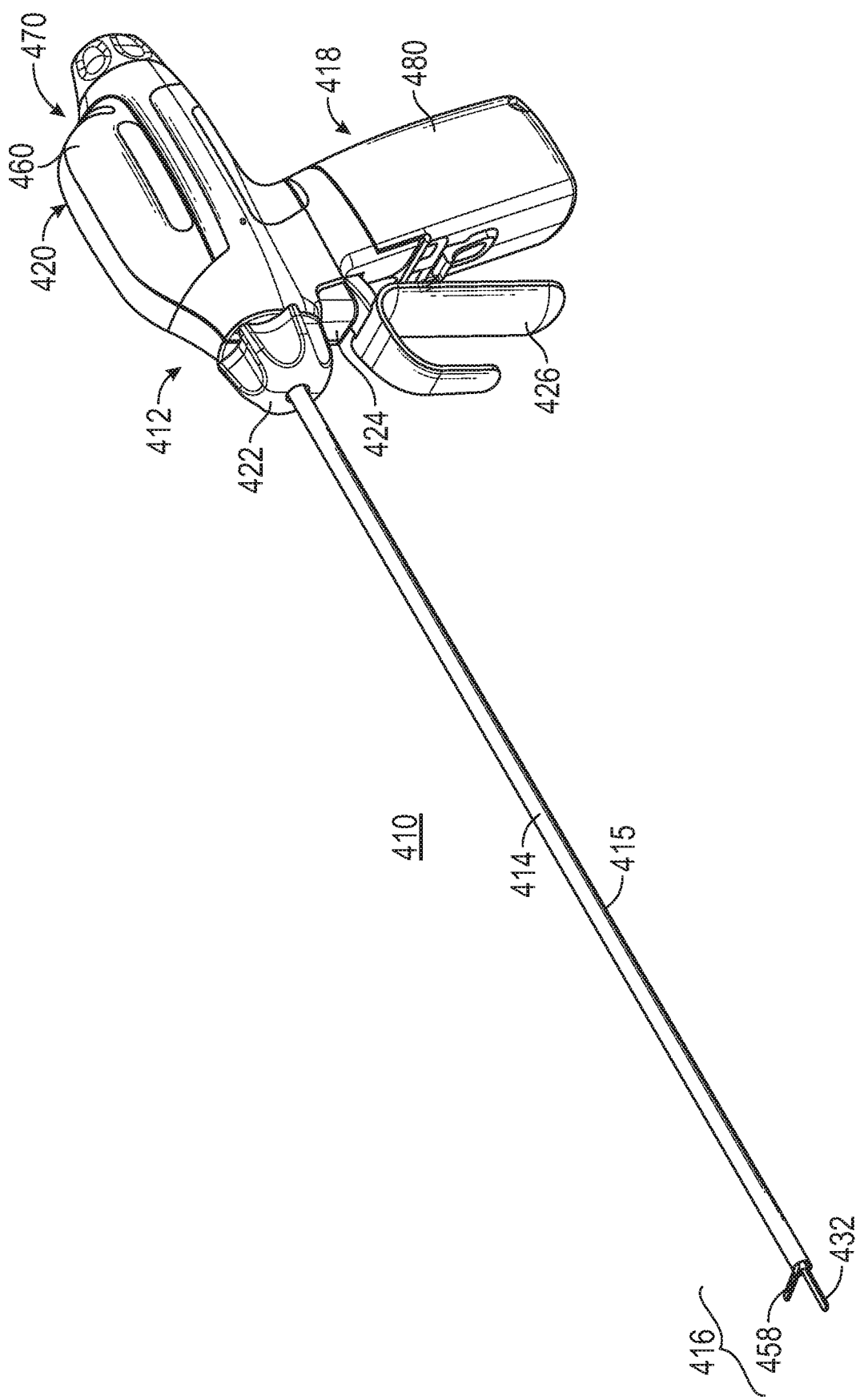
FIG. 1D is a perspective view of an ultrasonic surgical instrument including an on-board generator, power source, and transducer provided in accordance with the present disclosure.

Referring now to FIG. 1D, an ultrasonic surgical instrument 410 generally includes a handle assembly 412, an elongated body portion 414, and a tool assembly 416. Tool assembly 416 includes a blade 432 and a clamp member 458. Handle assembly 412 supports a battery assembly 418 and an ultrasonic transducer and generator assembly ("TAG") 420, and includes a rotatable nozzle 422, an activation button 424, and a clamp trigger 426. Battery assembly 418 and TAG 420 are each releasably secured to handle assembly 412, and are removable therefrom to facilitate disposal of the entire device, with the exception of battery assembly 418 and TAG 420. However, it is contemplated that any or all of the components of ultrasonic surgical instrument 410 be configured as disposable single-use components or sterilizable multi-use components. Further, ultrasonic surgical instrument 410 may be configured to connect to a remote generator and/or power source, rather than having such components on-board.

With continued reference to FIG. 1D, elongated body portion 414 includes an outer shaft assembly 415 and waveguide (not shown) which extends distally from handle assembly 412 through outer shaft assembly 415 to tool assembly 416. A distal end of the waveguide defines a blade 432. A proximal end of the waveguide is configured to engage TAG 420, as detailed below. The waveguide and outer shaft assembly 415 are rotatably coupled to rotatable nozzle 422 such that rotation of nozzle 422 effects corresponding rotation of the outer shaft assembly 415 and the waveguide. The outer shaft assembly 415 includes a support tube and an actuator tube which are disposed about one another in either configuration The actuator tube of outer shaft assembly 415 is configured to move relative to the support tube of outer shaft assembly 415 to enable pivoting of clamp member 458 between an open position, wherein clamp member 458 is spaced from blade 432, and a closed position, wherein clamp member 458 is approximated relative to blade 432. Clamp member 458 is moved between the open and closed positions in response to actuation of clamp trigger 426.

Continuing with reference to FIG. 1D, activation button 424 is supported on handle assembly 412. When activation button 424 is activated in an appropriate manner, an underlying two-mode switch assembly is activated to effect communication between battery assembly 418 and TAG 420 in either a "LOW" power mode or a "HIGH" power mode, depending upon the manner of activation of activation button 424.

TAG 420 includes a generator 470 and an ultrasonic transducer (not shown). Generator 470 includes an outer housing 460 that houses a TAG microcontroller having a memory. TAG 420 supports the ultrasonic transducer thereon. The ultrasonic transducer may include a piezoelectric stack and defines a forwardly extending horn configured to engage the proximal end of the waveguide. A series of contacts (not explicitly shown) associated with TAG 420 enable communication of power and/or control signals between TAG 420, battery assembly 418, and the two-mode switch assembly, although contactless communication therebetween is also contemplated.

In general, in use, when battery assembly 418 and TAG 420 are attached to handle assembly 412 and waveguide 430, respectively, and ultrasonic surgical instrument 410 is activated, battery cells of battery assembly 418 provide power to generator 470 of TAG 420 which, in turn, uses this power to apply an AC signal to the ultrasonic transducer of TAG 420. The ultrasonic transducer, in turn, converts the AC signal into high frequency mechanical motion. This high frequency mechanical motion produced by the ultrasonic transducer is transmitted along the waveguide to the blade 432 for application of such ultrasonic energy to tissue adjacent to or clamped between blade 432 and clamp member 458 to treat tissue.

Figure 2:
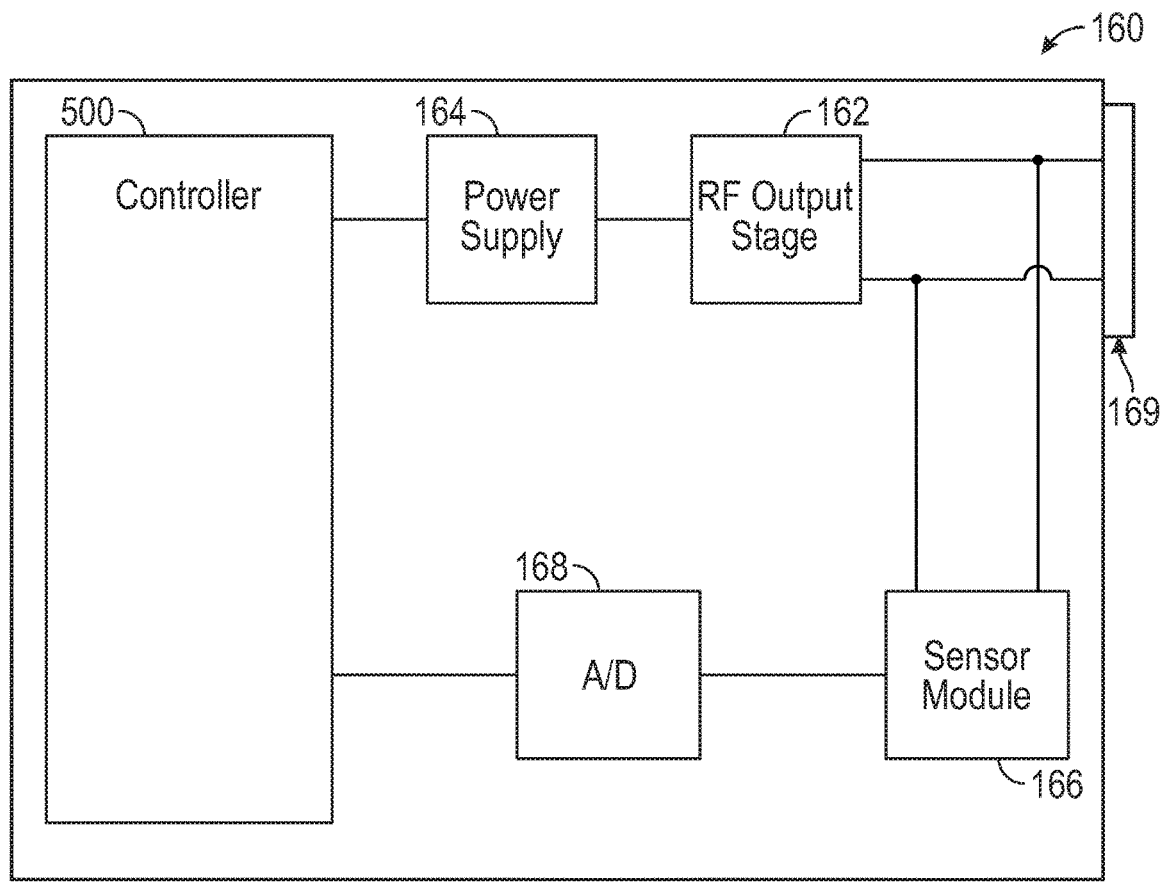
FIG. 2 is a block diagram of the generator of the systems of FIGS. 1A and 1B.

Referring now to FIG. 2, there is shown a block diagram of exemplary components of an electrosurgical generator 160 in accordance with aspects of the disclosure. In the illustrated embodiment, the generator 160 includes a controller 500, a power supply 164, a radio-frequency (RF) energy output stage 162, a sensor module 166, and one or more connector ports 169 that accommodate various types of electrosurgical instruments. The generator 160 can include a user interface (not shown), which permits a user to select various parameters for the generator 160, such as mode of operation and power setting. In various embodiments, the power setting can be specified by a user to be between zero and a power limit, such as, for example, five watts, thirty watts, seventy watts, or ninety-five watts.

The electrosurgical generator 160 may be any suitable type of generator and may include a plurality of connectors to accommodate various types of electrosurgical instruments (e.g., monopolar electrosurgical instrument and bipolar electrosurgical instrument). The electrosurgical generator 160 may also be configured to operate in a variety of modes, such as ablation, cutting, coagulation, and sealing. The electrosurgical generator 160 may include a switching mechanism (e.g., relays) to switch the supply of RF energy among the connectors 169 to which various electrosurgical instruments may be connected. For example, when an electrosurgical instrument, e.g., forceps 100 (FIG. 1A) or forceps 200 (FIG.

1B), is connected to the electrosurgical generator 160, the switching mechanism switches the supply of RF energy to the monopolar plug 169. In embodiments, the electrosurgical generator 160 may be configured to provide RF energy to a plurality instruments simultaneously.

In various embodiments the generator 160 may include a sensor module 166 which includes a plurality of sensors, e.g., an RF current sensor, and an RF voltage sensor. Various components of the generator 160, namely, the RF output stage 162 and the RF current and voltage sensors of sensor module 166 may be disposed on a printed circuit board (PCB). The RF current sensor of sensor module 166 may be coupled to the active terminal and provides measurements of the RF current supplied by the RF output stage 162. In embodiments the RF current sensor of sensor module 166 may be coupled to the return terminal. The RF voltage sensor of sensor module 166 is coupled to the active and return terminals and provides measurements of the RF voltage supplied by the RF output stage 162. In embodiments, the RF current and voltage sensors of sensor module 166 may be coupled to active and return leads and, which interconnect the active and return terminals and to the RF output stage 162, respectively.

The RF current and voltage sensors of the sensor module 166 sense and provide the sensed RF voltage and current signals, respectively, to the controller 500 of generator 160, which then may adjust output of the power supply and/or the RF output stage 162 in response to the sensed RF voltage and current signals. Controller 500 is described in greater detail hereinbelow (see FIG. 5).

The sensed voltage and current from sensor module 166 are fed to analog-to-digital converters (ADCs) 168. The ADCs 168 sample the sensed voltage and current to obtain digital samples of the voltage and current of the RF output stage 162. The digital samples are processed by the controller 500 and used to generate a control signal to control the DC/AC inverter of the RF output stage 162 and the preamplifier. The ADCs 168 communicate the digital samples to the controller 500 for further processing.

Figure 3:
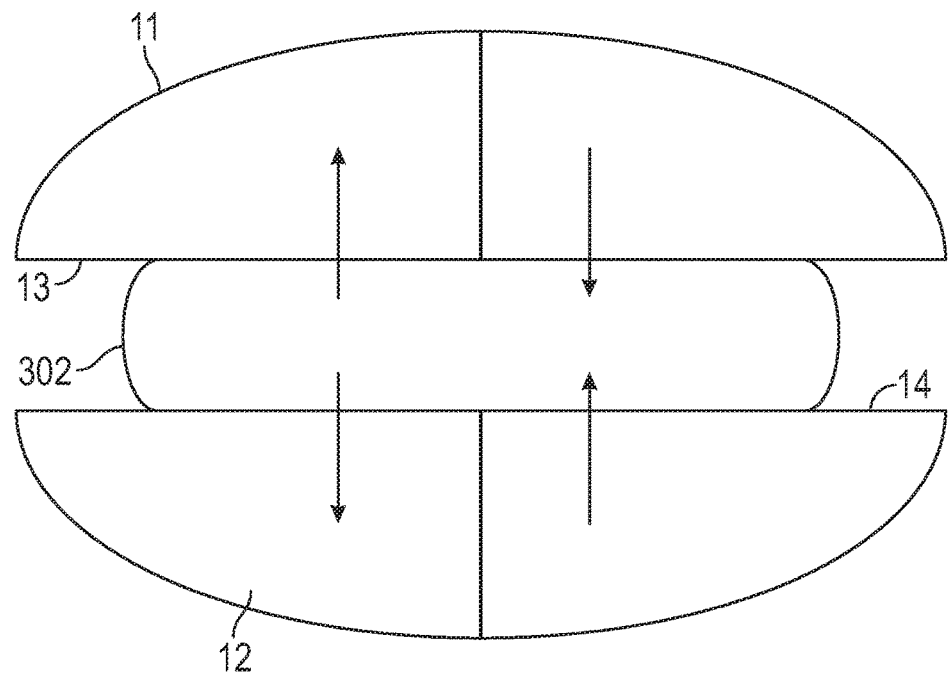
FIG. 3 is a transverse, cross-sectional view of the end effector assembly of the energy-based surgical instrument of the surgical system of FIG. 1A, shown grasping and applying energy to tissue.

Referring now to FIG. 3, a transverse, cross-sectional view of the end effector assembly 10 of forceps 100 of FIG. 1A is shown. Jaw members 11, 12 grasp tissue 302 between the electrically conductive surfaces 13, 14 of the jaw members 11, 12. Generator 160 (FIG. 2) supplies electrosurgical energy to electrically conductive surfaces 13, 14 at different potentials such that electrosurgical energy is conducted therebetween and through the grasped tissue 302 to heat and thereby treat, e.g., seal, the tissue 302. As noted above, by controlling the application of energy from the generator 160 (FIG. 2) to surfaces 13, 14, the heating of the tissue 302 can be controlled to achieve a tissue seal. As also noted above, the disclosure provides systems and methods for estimating tissue temperature, e.g., for use in controlling the application of energy to the tissue 302, using available data and without the need for temperature sensors.

Figure 4:
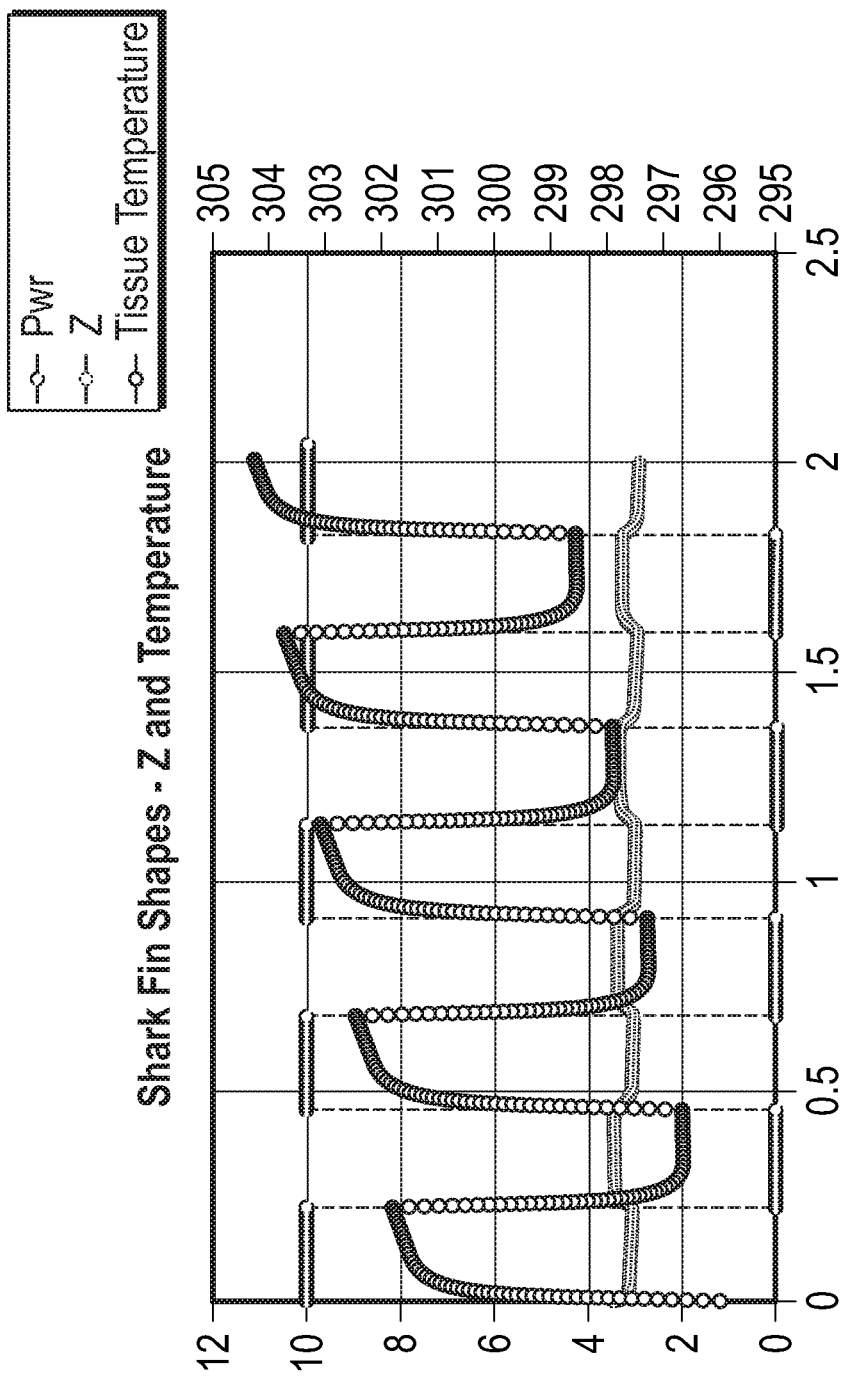
FIG. 4 is an exemplary power, impedance, and temperature versus time graph during the course of treatment of tissue using the surgical system of FIG. 1A.

FIG. 4 shows a graph of how tissue temperature is related to the power applied to the tissue and the tissue impedance when a pulse of RF energy is applied to the tissue 302 (FIG. 3). Referring also to FIG. 3, for example, a pulse of RF energy is applied to tissue 302 grasped between electrically conductive tissue treating surfaces 13, 14 of jaw members 11, 12. While power is applied, the temperature of the tissue increases with a "shark fin" temperature shape and the impedance of tissue decreases with a corresponding shape. This "shark fin" impedance shape which results from the pulse of RF energy contains information about the tissue mass and surface area that is in contact with electrically conductive tissue treating surfaces 13, 14 of jaw members 11, 12, as well as the heat transfer characteristics of the tissue and the jaw members 11, 12. This is due to heat flow between the tissue, the jaw seal plates, insulator and handset and then to the environment. This heat flow is affected by the tissue mass and the tissue surface area contacting the jaw. Tissue impedance changes due to temperature related changes in saline conductivity.

Figure 5:
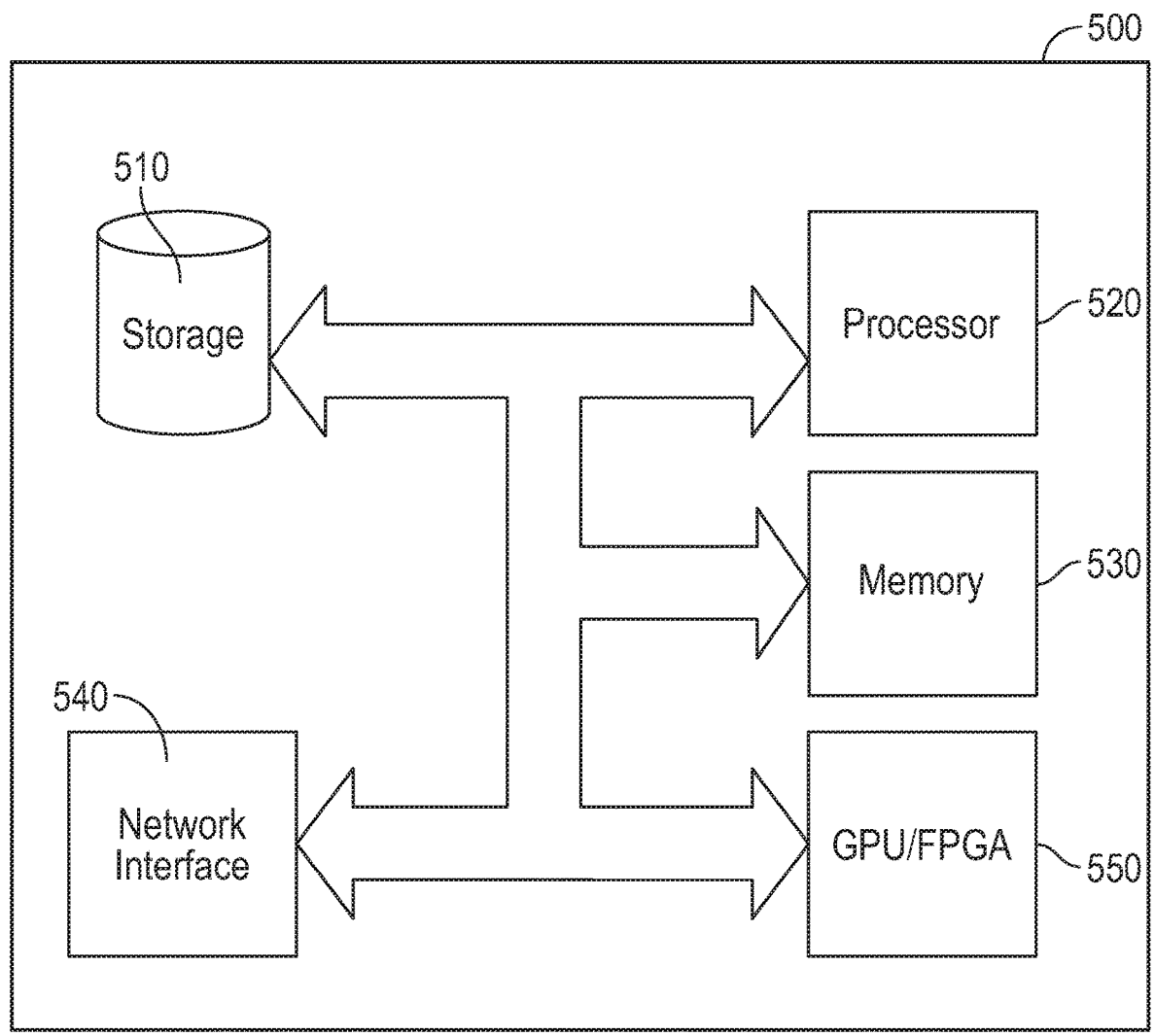
FIG. 5 is a block diagram of a controller provided in accordance with the disclosure and configured for use with the surgical system of FIG. 1A.

Referring to FIG. 5, the controller 500 in accordance with the disclosure is shown. The controller 500 includes a processor 520 connected to a computer-readable storage medium or a memory 530 which may be a volatile type memory, e.g., RAM, or a non-volatile type memory, e.g., flash media, disk media, etc. In various embodiments, the processor 520 may be another type of processor such as, without limitation, a digital signal processor, a microprocessor, an ASIC, a graphics processing unit (GPU), field-programmable gate array (FPGA), or a central processing unit (CPU). In various embodiments, network inference may also be accomplished in systems that may have weights implemented as memistors, chemically, or other inference calculations, as opposed to processors.

In various embodiments, the memory 530 can be random access memory, read only memory, magnetic disk memory, solid state memory, optical disc memory, and/or another type of memory. In various embodiments, the memory 530 can be separate from the controller 500 and can communicate with the processor 520 through communication buses of a circuit board and/or through communication cables such as serial ATA cables or other types of cables. The memory 530 includes computer-readable instructions that are executable by the processor 520 to operate the controller 500. In various embodiments, the controller 500 may include a network interface 540 to communicate with other computers or a server. In embodiments, a storage device 510 may be used for storing data. In various embodiments, the controller 500 may include one or more FPGAs 550. The FPGA 550 may be used for executing various machine learning algorithms such as those provided in accordance with the disclosure, as detailed below.

The memory 530 stores suitable instructions, to be executed by the processor 520, for receiving the sensed data, e.g., sensed data from sensor module 166 via ADCs 168 (see FIG. 2), accessing storage device 510 of the controller 500, determining one or more tissue parameters, e.g., tissue temperature, based upon the sensed data and information stored in storage device 510, and providing feedback based upon the determined tissue parameters. Although illustrated as part of generator 160, it is also contemplated that controller 500 be remote from generator 160, e.g., on a remote server, and accessible by generator 160 via a wired or wireless connection. In embodiments where controller 500 is remote, it is contemplated that controller 500 may be accessible by and connected to multiple generators 160.

Storage device 510 of controller 500 stores one or more machine learning algorithms and/or models, configured to estimate one or more tissue parameters, e.g., tissue temperature, based upon the sensed data received from sensory circuitry, e.g., from sensor module 166 via ADCs 168 (see FIG. 2). The machine learning algorithm(s) may be trained on and learn from experimental data and/or data from previous procedures initially input into the one or more machine learning applications in order to enable the machine learning application(s) to estimate the tissue parameters based upon such data. Such data may include tissue impedance data, power data, time, and/or any other suitable data. Such estimated tissue parameters may include tissue temperature, tissue mass, tissue surface area, steam formation/release, collagen denaturing, tissue pressure, collagen/gelatin flow, tissue size/mass changes, and tissue water content.

Referring generally to FIGS. 2-5, machine learning algorithms are advantageous for use in determining tissue parameters at least in that complex sensor components and pre-defined categorization rules and/or algorithms are not required. Rather, machine learning algorithms utilizes the initially input data, e.g., the previous procedure data and/or experimental data, to determine statistical features and/or correlations that enable the determination of tissue parameters of unknown tissues by analyzing data therefrom. Thus, with the one or more machine learning algorithms having been trained as detailed above, such can be used to determine parameters of tissue being treated, e.g., using end effector assembly 10. More specifically, processor 520 of controller 500 is configured, in response to receiving sensed data from sensory circuitry, e.g., from sensor module 166 via ADCs 168, to input the sensed data into the machine learning algorithm(s) stored in storage device 510 in order to determine the one or more tissue parameters of the tissue being treated using end effector assembly 10. Although described with respect to an electrosurgical system, the aspects and features of controller 500 and the machine learning algorithms configured for use therewith are equally applicable for use with other suitable surgical systems, e.g., an ablation system 1100 (FIG. 1C) and/or an ultrasonic system 400 (FIG. 1D).

Once the tissue parameters are determined by the controller 500, depending upon the tissue parameters, settings, user input, etc., controller 500 may for example, output an alert and/or warning to user interface, implement, switch, or modify a particular energy-delivery algorithm based upon which the power supply 164 and RF output stage 162 provide energy to end effector assembly 10, and/or inhibit further energy delivery to end effector assembly 10.

The terms "artificial intelligence," "data models," or "machine learning" may include, but are not limited to, neural networks, recurrent neural networks (RNN), generative adversarial networks (GAN), Bayesian Regression, Naive Bayes, nearest neighbors, least squares, means, and support vector regression, among other data science and artificial science techniques. Exemplary uses are identifying patterns and making predictions relating to calendar scheduling, including priority, length and due dates of time consumers, which will be described in more detail hereinbelow.

The term "application" may include a computer program designed to perform particular functions, tasks, or activities for the benefit of a user. Application may refer to, for example, software running locally or remotely, as a stand-alone program or in a web browser, or other software which would be understood by one skilled in the art to be an application. An application may run on the controller 500 or on a user device, including for example, on a mobile device, an IOT device, or a server system.

Figure 6A:
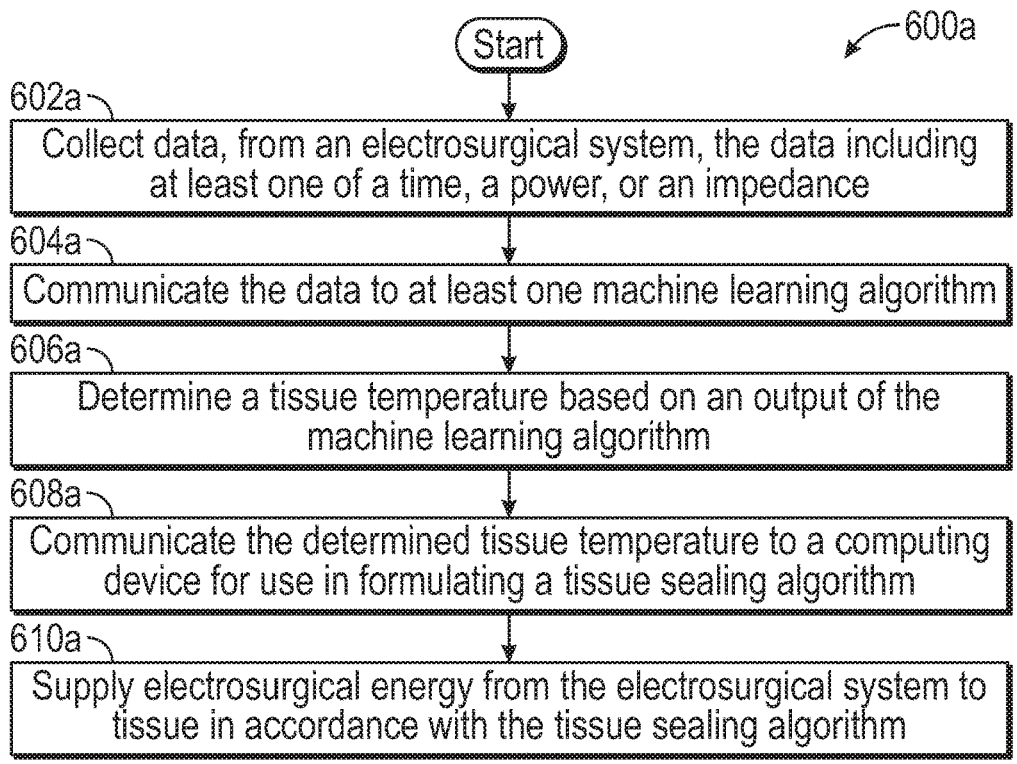
FIG. 6A is a flowchart of a method for estimating tissue parameters in accordance with the disclosure.

Referring now to FIG. 6A, there is shown a flow diagram of a computer implemented method 600a for method for estimating tissue parameters. Persons skilled in the art will appreciate that one or more operations of the method 600a may be performed in a different order, repeated, and/or omitted without departing from the scope of the disclosure. In various embodiments, the illustrated method 600a can operate in the controller 500 (FIG. 5), in a remote device, or in another server or system. In embodiments, some or all of the operations in the illustrated method 600a can operate using an electrosurgical system, e.g., instrument 100 or 200 and the generator 160 (see FIGS. 1A and 1B). Other variations are contemplated to be within the scope of the disclosure. The operations of FIG. 6A will be described with respect to a controller, e.g., controller 500 of generator 160 (FIGS. 2 and 5), but it will be understood that the illustrated operations are applicable to other systems and components thereof as well.

Initially at step 602a, the controller may collect data, from an electrosurgical system, including time, power, and/or impedance. For example, the electrosurgical system may include a generator and an electrosurgical instrument such as detailed above with respect to FIGS. 1A and 1B. While a surgeon is operating the electrosurgical system during surgery, they may use the system to apply electrosurgical (RF) energy to tissue to treat tissue. More specifically, with additional reference to FIG. 2, tissue 302 is grasped between electrically conductive tissue treating surfaces 13, 14 of jaw members 11, 12 (or jaw members 21, 22 of FIG. 1B) and electrosurgical (RF) energy is conducted between tissue treating surfaces 13, 14 and through tissue 302 to heat and thereby treat tissue 302. During such tissue treatment, the sensor circuitry, e.g., sensor module 166, of the generator 160 may sense parameters of the tissue and/or energy such as, for example, impedance and power, and/or may supply data from which impedance and/or power can be derived such as for example, time, voltage, and/or current data. It is contemplated that pressure may also be sensed or determined. This may occur as a snapshot or over a time interval and may be determined at the beginning of tissue treatment, e.g., at or within 250 ms of initiation of tissue treatment, to avoid permanent damage to tissue should it be determined that treatment should be discontinued. The sensed data may include, for example, time that the power is applied for, power applied to the tissue, and/or impedance of the tissue. The sensor module 166 may measure data from the electrosurgical system, for example, the voltage and/or a current of the electrosurgical energy being delivered to the tissue. In various embodiments, the voltage and the current may be used to derive the power or the impedance. This sensed data obtained by the sensor circuitry is relayed to the controller 500 (via the ADC's 168, in embodiments) for further processing, as detailed below.

In step 604a, the controller communicates the data as an input to a machine learning algorithm, e.g., a neural network. In embodiments, training the neural network may be accomplished by identifying patterns in the impedance curve shape and/or a power versus time curve. In various embodiments, a neural network may be used for training data, for example: impedance, power, time, tissue electrical properties, tissue thermal properties, electrosurgical device electrical properties, or electrosurgical device thermal properties of the jaw members 11, 12 (FIG. 1A) or jaw members 21, 22 (FIG. 1B), may be used as input data. In various embodiments, the outputs of the neural network may be used as training data for supervised learning. It is contemplated that the training may be performed on a separate system, for example GPU servers, simulation, etc., and the trained network would then be deployed in the electrosurgical system 1100.

In step 606a, the controller determines the tissue parameter, e.g., tissue temperature, based on the output of the machine learning algorithm. In various embodiments, the controller may additionally or alternatively determine the tissue mass and/or the tissue surface area based on the machine learning algorithm. In various embodiments, the machine learning algorithm may be a neural network. In various embodiments, the neural network may use supervised learning, unsupervised learning, or reinforcement learning. In various embodiments, the neural network may include a temporal convolutional network or a feed forward network.

In various embodiments, the neural network may include a three-layer temporal convolutional network with residual connections, where each layer may include three parallel convolutions, where the number of kernels and dilations increase from bottom to top, and where the number of convolutional filters increase from bottom to top. It is contemplated that a higher or lower amount of layers may be used. It is contemplated that a higher or lower number of kernels and dilations may also may be used. In various embodiments, the machine learning algorithm may output a tissue temperature, a tissue mass, and/or a tissue temperature for the tissue being treated.

At step 608a, the controller communicates the determined tissue temperature that was output from the machine learning algorithm to a computing device, e.g., of controller 500, for use in formulating, e.g., switching, confirming, modifying, generating, etc., a tissue sealing algorithm.

At step 610a, the controller supplies electrosurgical energy from the electrosurgical system to the tissue to be treated, in accordance with the tissue sealing algorithm. In various embodiments, a continuous burst pressure predictor or a thermal spread predictor may be fed from the outputs of step 608. In various embodiments, training the machine learning algorithm may be performed by a computing device outside of the generator 160 and the resulting algorithm may be communicated to the controller 500 of generator 160.

Figure 6B:
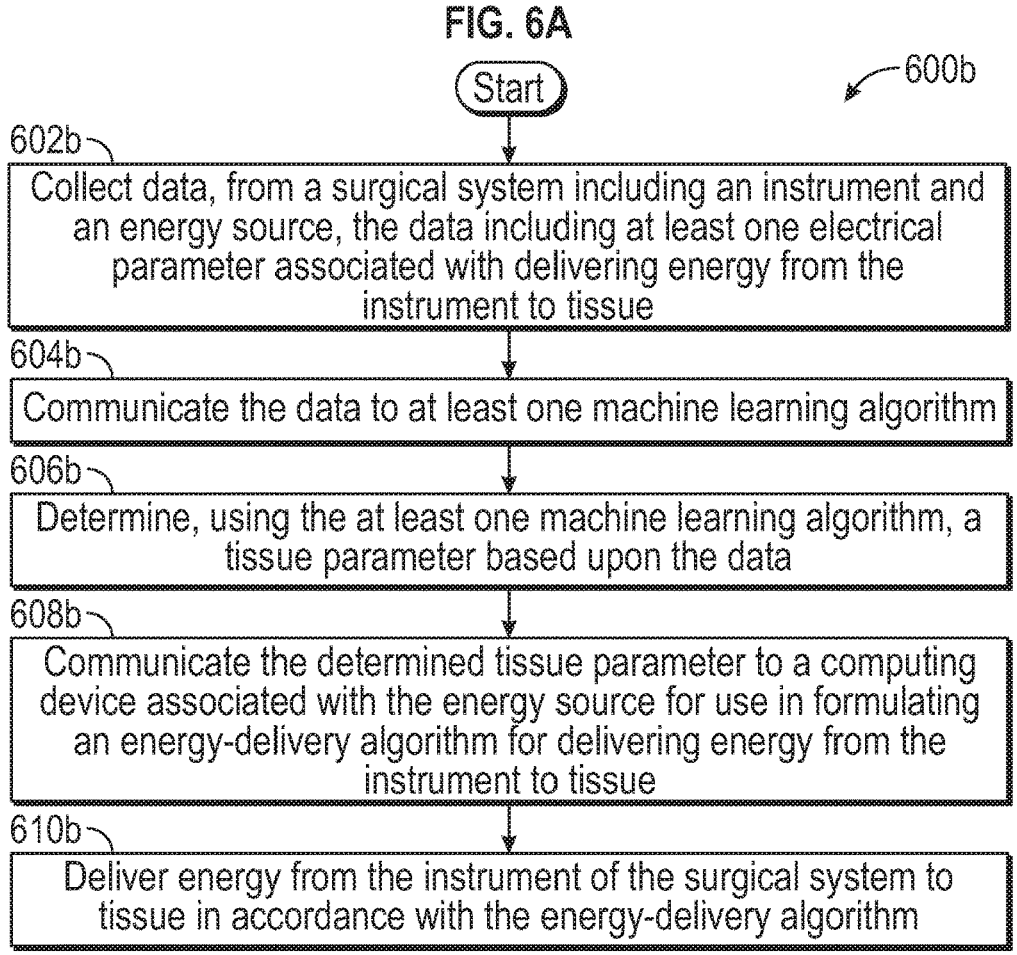
FIG. 6B is a flowchart of another method for estimating tissue parameters in accordance with the disclosure.

Referring now to FIG. 6B, there is shown a flow diagram of a computer implemented method 600 for method for estimating tissue parameters. Persons skilled in the art will appreciate that one or more operations of the method 600b may be performed in a different order, repeated, and/or omitted without departing from the scope of the disclosure. In various embodiments, the illustrated method 600b can operate in the controller 500 (FIG. 5), in a remote device, or in another server or system. In various embodiments, some or all of the operations in the illustrated method 600b can operate using an electrosurgical system, e.g., instrument 100 or 200 and the generator 160 (see FIGS. 1A and 1B). Other variations are contemplated to be within the scope of the disclosure. The operations of FIG. 6B will be described with respect to a controller, e.g., controller 500 of generator 160 (FIGS. 2 and 5), but it will be understood that the illustrated operations are applicable to other systems and components thereof as well.

Initially at step 602b, the controller may collect data, from a surgical system. The system includes an instrument and an energy source. The data may include one or more electrical parameters associated with delivering energy from the instrument to the tissue. For example, the surgical system may include an electrosurgical generator and an electrosurgical instrument such as detailed above with respect to FIGS. 1A and 1B. As another example, the system may be a microwave ablation system or an ultrasonic surgical instrument such as detailed above with respect to FIGS. 1C and 1D. While a surgeon is operating the electrosurgical system during surgery, they may use the system to apply electrosurgical (e.g., RF, MW, or US) energy to tissue to treat tissue. More specifically, with additional reference to FIG. 2, tissue 302 is grasped between electrically conductive tissue treating surfaces 13, 14 of jaw members 11, 12 (or jaw members 21, 22 of FIG. 1B) and electrosurgical (e.g., RF or US) energy is conducted between tissue treating surfaces 13, 14 and through tissue 302 to heat and thereby treat tissue 302. During such tissue treatment, the sensor circuitry, e.g., sensor module 166, of the generator 160 may sense parameters of the tissue and/or energy such as, for example, impedance and power, and/or may supply data from which impedance and/or power can be derived such as for example, frequency time, voltage, and/or current data. It is contemplated that pressure may also be sensed or determined. This may occur as a snapshot or over a time interval and may be determined at the beginning of tissue treatment, e.g., at or within 250 ms of initiation of tissue treatment, to avoid permanent damage to tissue should it be determined that treatment should be discontinued. The sensed data may include, for example, time that the power is applied for, power applied to the tissue, and/or impedance of the tissue. The sensor module 166 may measure data from the electrosurgical system, for example, the voltage and/or a current of the electrosurgical energy being delivered to the tissue. In various embodiments, the voltage and the current may be used to derive the power or the impedance. In various embodiments, a Hall effect power meter may be used to derive the power or the impedance. This sensed data obtained by the sensor circuitry is relayed to the controller 500 (via the ADC's 168, in embodiments) for further processing, as detailed below. With reference to FIG. 1C, the sensor data may include measuring the temperature of the balun or choke of the probe, the reflected power, or tissue temperature. With reference to FIG. 1D, the sensors may also measure the temperature of the transformer, the temperature of the blade, the frequency of the blade movement, and blade temperature, tissue temperature, and/or tissue division.

In step 604b, the controller communicates the data as an input to a machine learning algorithm, e.g., a neural network. In embodiments, training the neural network may be accomplished by identifying patterns in the impedance curve shape and/or a power versus time curve. In various embodiments, a neural network may be used for training data, for example: impedance, power, time, frequency, current, voltage, tissue electrical properties, tissue thermal properties, shape of the instrument, electrical properties of the instrument, or thermal properties of the jaw members 11, 12 (FIG. 1A), jaw members 21, 22 (FIG. 1B), probe 1112, 1112', (FIG. 1C), or the clamp components 458, 432 (FIG. 1D).

In step 606b, the controller determines a tissue parameter, e.g., tissue temperature, or tissue type, based on the output of the machine learning algorithm. In various embodiments, the controller may additionally or alternatively determine the tissue mass and/or the tissue surface area based on the machine learning algorithm. In various embodiments, the machine learning algorithm may be a neural network. In various embodiments, the neural network may use supervised learning, unsupervised learning, or reinforcement learning. In various embodiments, the neural network may include a temporal convolutional network or a feed forward network.

In various embodiments, the neural network may include a three-layer temporal convolutional network with residual connections, where each layer may include three parallel convolutions, where the number of kernels and dilations increase from bottom to top, and where the number of convolutional filters increase from bottom to top. It is contemplated that a higher or lower amount of layers may be used. In various embodiments, the machine learning algorithm may output a tissue temperature, a tissue mass, and/or a surface area for the tissue being treated.

At step 608b, the controller communicates the determined tissue parameter that was output from the machine learning algorithm to a computing device, e.g., of controller 500, for use in formulating, e.g., switching, confirming, modifying, generating, etc., an energy delivery algorithm. In an embodiment, the tissue temperature may be determined without a temperature sensor.

At step 610*b*, the controller supplies electrosurgical energy from the electrosurgical system to the tissue to be treated, in accordance with the energy delivery algorithm. In various embodiments such as, for example, vessel sealing applications, a continuous burst pressure predictor may be fed from the outputs of step 608*b*. With respect to ablation applications, as another example, an ablation zone volume may be fed from the outputs of step 608*b*. However, it is understood that other suitable outputs may be provided depending, for example, upon the particular application. In various embodiments, training the machine learning algorithm may be performed by a computing device outside of the generator 160 and the resulting algorithm may be communicated to the controller 500 of generator 160.

Figure 7:
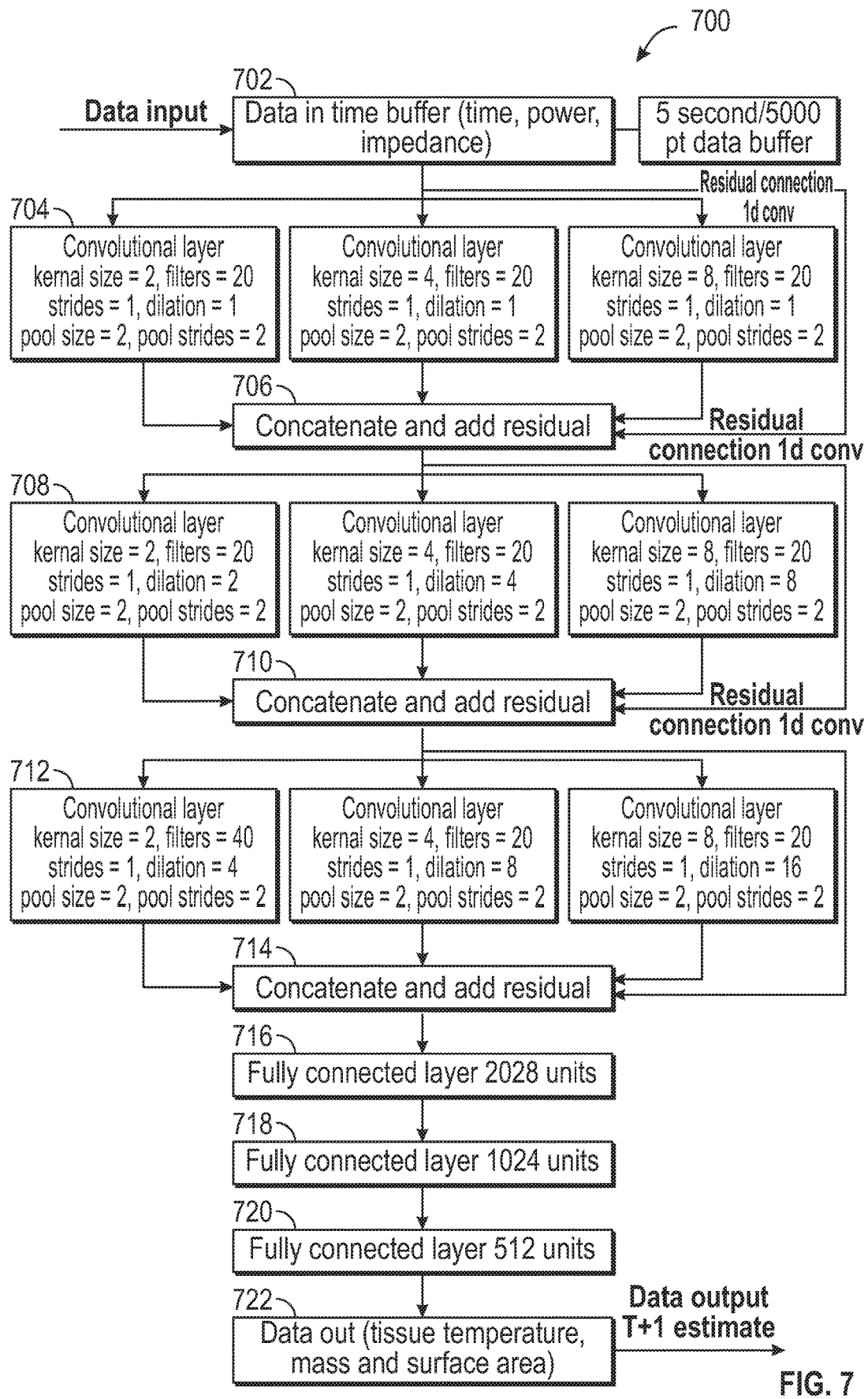
FIG. 7 is a flowchart of a machine learning algorithm in accordance with the disclosure.

FIG. 7 depicts an embodiment of a machine learning algorithm 700 in accordance with the disclosure. In various embodiments, the machine learning algorithm 700 may be a three-layer temporal convolution network with residual connections. Each layer has three parallel convolutions with varying kernel filter sizes. Kernels and dilations increase from bottom to top. The number of convolutional filters increases from bottom to top of the machine learning algorithm 700.

At step 702, sampled time, power, and impedance are entered as input data. In various embodiments, there may be a 5 second, 5000-point data buffer. At step 704, three convolutional layers are fed in parallel. In various embodiments, the first the convolutional layer may have, for example, a kernel size of 2, while the second has a kernel size of 4 and the third has a kernel size of 8. A kernel size may be either an integer or a list of integers which specify the length of the convolution window. A residual connection may be a convolutional kernel that is convolved with the layer input over a single spatial (or temporal) dimension to produce tensor outputs. At step 706, the resulting data from step 704 is concatenated and the residual is added.

At step 708, three convolutional layers are fed in parallel with the data resulting from step 706. In various embodiments, the first the convolutional layer may have, for example, a kernel size of 2, while the second has a kernel size of 4 and the third has a kernel size of 8. A residual connection may be a convolutional kernel that is convolved with the layer input over a single spatial (or temporal) dimension to produce tensor outputs. At step 710, the resulting data from step 708 is concatenated and the residual is added. This may be repeated a third time for steps 712 and 714. It is contemplated that more than three layers may be used.

At step 716, through 720, three fully connected layers may be used. A fully connected layer creates a fully connected weight matrix. This weight matrix may be multiplied by the inputs from 714, to produce a tensor. At step 722, the resultant outputs of tissue mass, tissue temperature and tissue surface area are then sent to the sealing algorithm. The machine learning algorithm 700 then moves to the next sample and repeats the process.

Figure 8:
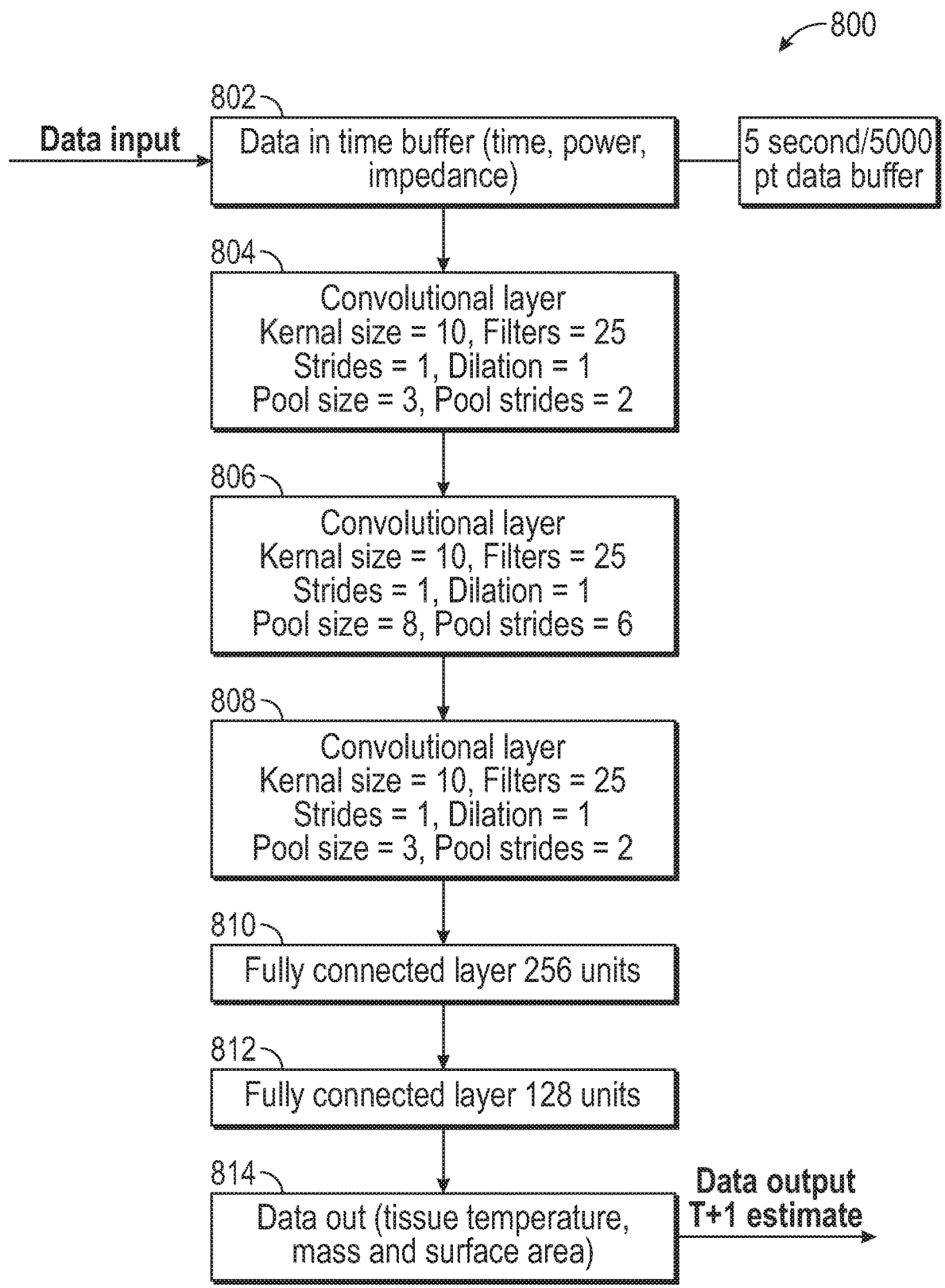
FIG. 8 is a flowchart of another a machine learning algorithm in accordance with the disclosure.

FIG. 8 depicts a second embodiment of a machine learning algorithm 800 in accordance with the disclosure. In various embodiments, the machine learning algorithm 800 may be a three-layer temporal convolution network with residual connections. Each layer has three parallel convolutions. Kernels and dilations increase from bottom to top. The number of convolutional filters increases from bottom to top of the machine learning algorithm 700.

At step 802, sampled time, power, and impedance are entered as input data. In various embodiments, there may be a 5 second, 5000-point data buffer. At step 804, three convolutional layers are fed in series. In various embodiments, the convolutional layers may have a kernel size of 10. Filters as shown in step 804 through 808 are the dimensionality of the output space, i.e. the number of output filters in the convolution. For example, at step 804 there are 25 output filters in the convolution. It is contemplated that any number of output filters may be used.

At step 810 and 812 two fully connected layers may be used. A fully connected layer creates a fully connected weight matrix. This weight matrix may be multiplied by the inputs from 808, to produce a tensor of hidden units.

At step 814, the resultant outputs of tissue mass, tissue temperature and tissue surface area are then sent to the sealing algorithm. The machine learning algorithm 800 then moves to the next sample and repeats the process.

Figure 9:
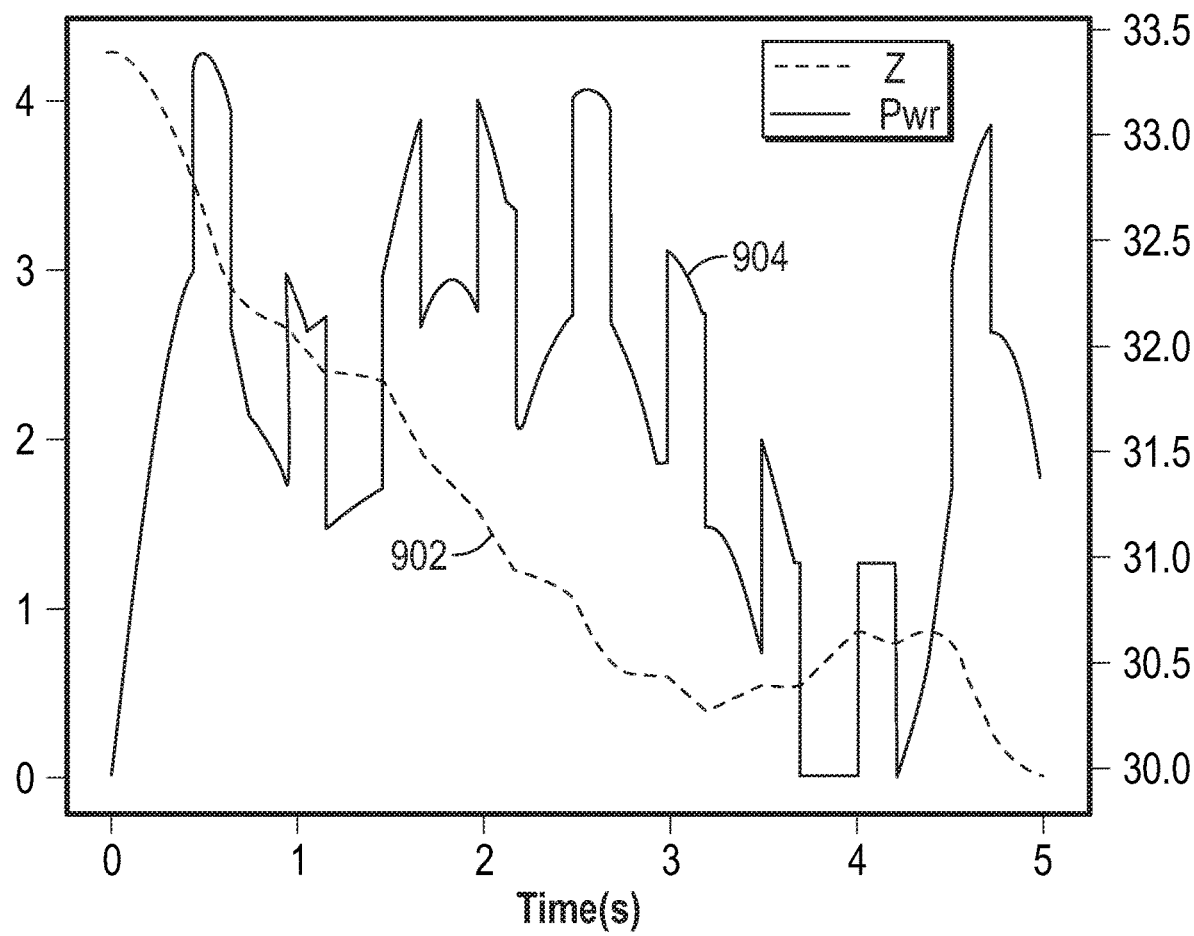
FIG. 9 is an exemplary power and impedance versus time graph depicting exemplary results of a machine learning algorithm of the disclosure.
Figure 10A:
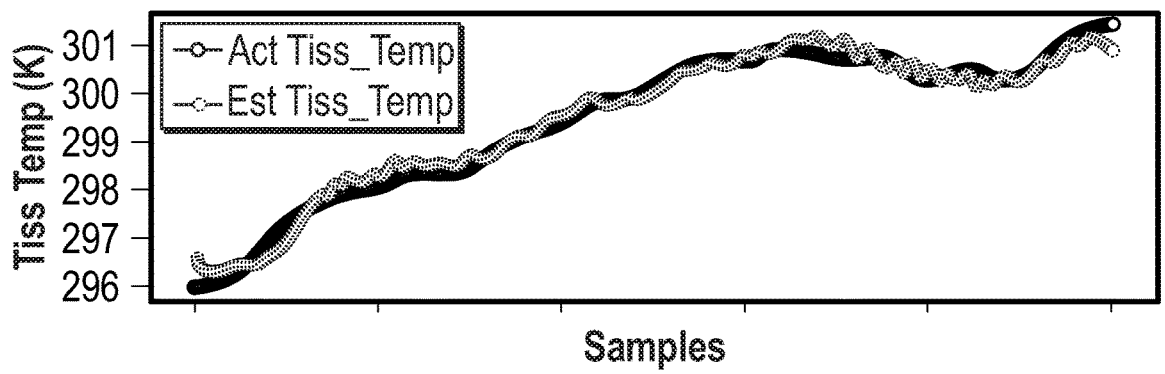
FIG. 10A is an exemplary graph of tissue temperature versus number of time steps comparing actual results with those obtained using a machine learning algorithm of the disclosure.
Figure 10B:
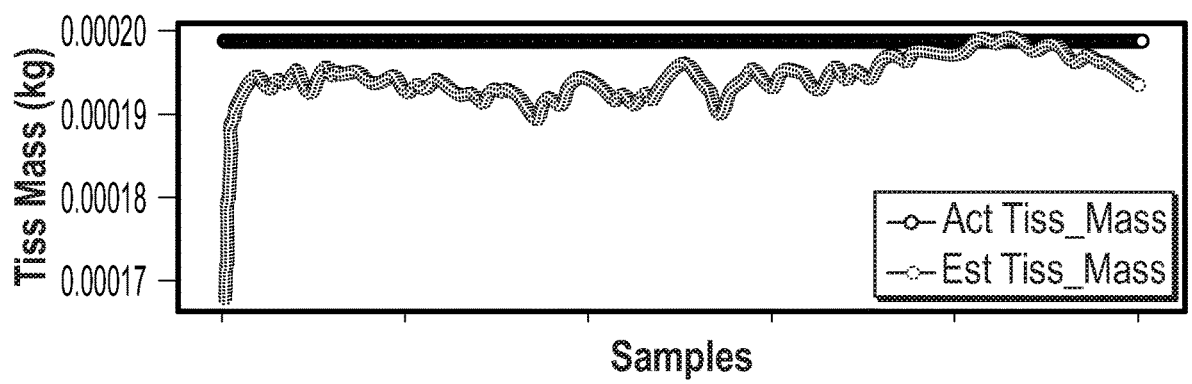
FIG. 10B is an exemplary graph of tissue mass versus number of time steps comparing actual results with those obtained using a machine learning algorithm of the disclosure.
Figure 10C:
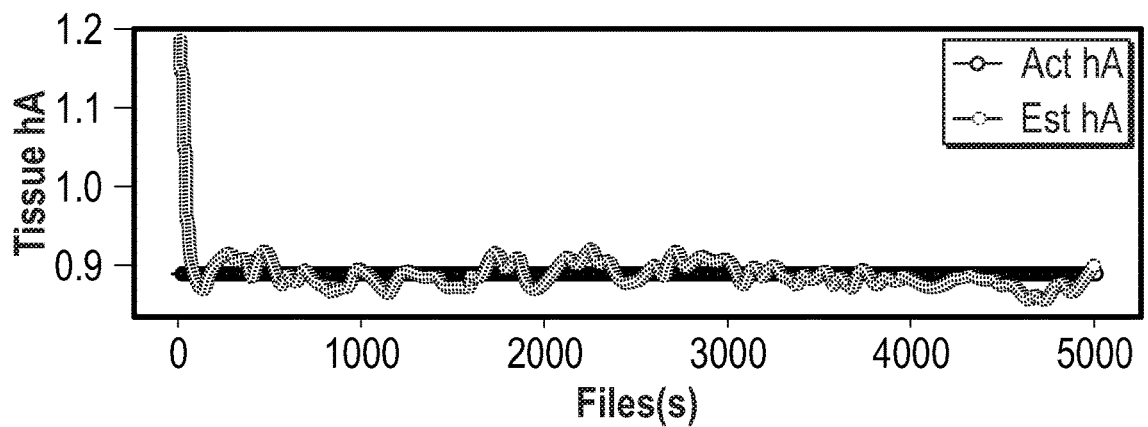
FIG. 10C is an exemplary graph of tissue surface area versus number of time steps comparing actual results with those obtained using a machine learning algorithm of the disclosure.

FIG. 9 and FIGS. 10A-10C are examples of results of the machine learning algorithms from FIG. 8. FIG. 9 is an exemplary power 904 and impedance 902 versus time graph depicting exemplary results in accordance with the disclosure. FIG. 10A is an exemplary graph of tissue temperature versus the number of input time steps to the machine learning algorithm during inference, in accordance with the disclosure. This set of plots represents the actual output of a trained network as compared to the actual outputs of a simulation. FIG. 10B is an exemplary graph of tissue mass versus the number of input time steps to the machine learning algorithm during inference, in accordance with the disclosure. FIG. 10C is an exemplary graph of tissue surface area versus the number of input time steps to the machine learning algorithm during inference. The graphs compare actual values to the estimates generated by the machine language algorithms. Actual values are representative of measured tissue parameters using, for example, tissue temperature sensors. As can be seen in FIG. 9 and FIGS. 10A-10C, the trained network now sees more history of how the tissue reacts to the power input. More history allows its predictions for this tissue/power profile to become more accurate. For example, at time 0 the network does not know what the tissue properties are. After 100 ms, the network now sees 100 ms worth of tissue reaction and thus can start predicting more accurately. After 1000 ms the network has even more examples of tissue reaction, thus the estimates improve.

From the foregoing and with reference to the various figure drawings, those skilled in the art will appreciate that certain modifications can also be made to the disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A computer implemented method for estimating tissue parameters, the computer implemented method comprising:
    collecting data, from a surgical system including an instrument and an energy source, the data including at least one observed electrical parameter associated with delivering energy from the instrument to tissue, wherein the at least one observed electrical parameter includes power over a period of time and an instantaneous impedance of the tissue;

communicating the data to at least one machine learning algorithm, wherein the at least one machine learning algorithm is trained using training data that includes at least one of an impedance versus time curve or a power versus time curve and corresponding tissue temperature or tissue pressure;

estimating, using the at least one machine learning algorithm, a tissue parameter based upon the at least one observed electrical parameter, wherein the estimated tissue parameter includes an estimated tissue temperature and an estimated tissue pressure;

communicating the estimated tissue parameter to a computing device associated with the energy source;

formulating an energy-delivery algorithm for delivering energy from the instrument to tissue based on the estimated tissue temperature and tissue pressure; and delivering energy from the instrument of the surgical system to tissue in accordance with the energy-delivery algorithm.

2. The method of claim 1, wherein collecting the data from the surgical system includes measuring at least one of a voltage, a current, or a frequency, and wherein the estimating occurs at or within 250 ms of initiation of tissue treatment.

3. The method of claim 1, wherein the at least one machine learning algorithm includes a neural network.

4. The method of claim 3, wherein the neural network includes at least one of a temporal convolutional network or a feed forward network.

5. The method of claim 4, wherein:

communicating the data to at least one machine learning algorithm includes shifting data into the machine learning algorithm one time step at a time; and estimating the tissue parameter includes estimating, by the machine learning algorithm, the tissue parameter one time step at a time.

6. The method of claim 3, wherein the method further includes training the neural network using one or more of observing sensor data or identifying patterns in data.

7. The method of claim 3, wherein the method further includes training the neural network using training data including at least one of: impedance, power, time, tissue electrical properties, tissue thermal properties, electrical properties of the instrument, thermal properties of the instrument, size of the instrument, shape of the instrument, frequency, voltage, current, balun temperature, or transformer temperature.

8. The method of claim 1, wherein the estimating the tissue parameter further includes determining at least one of tissue mass, tissue surface area, steam formation/release, collagen denaturing, collagen/gelatin flow, tissue size/mass changes, or tissue water content.

9. The method of claim 1, wherein the energy source is adapted to generate energy for treating tissue, the energy source including one or more output terminals which supply energy to the tissue, the one or more output terminals operatively connected to one or more supply lines, the energy source including one or more return terminals configured to return energy from the tissue, the return terminals being operatively connected to one or more return lines, wherein the surgical system further includes a cable housing a portion of the one or more supply lines and the one or more return lines; and wherein the instrument is operatively connected to the cable.

10. The method of claim 1, wherein the surgical system includes at least one of a microwave ablation system, an electrosurgical system, or an ultrasonic surgical instrument.

11. A system for estimating tissue parameters, the system comprising:

an electrosurgical system;

one or more processors; and at least one memory coupled to the one or more processors, the at least one memory having instructions stored thereon which, when executed by the one or more processors, cause the system to:

collect data, from a surgical system including an instrument and an energy source, the data including at least one observed electrical parameter associated with delivering energy from the instrument to tissue, wherein the at least one observed electrical parameter includes power over a period of time and an instantaneous impedance of the tissue;

communicate the data to at least one machine learning algorithm, wherein the at least one machine learning algorithm is trained using training data that includes at least one of an impedance versus time curve or a power versus time curve and corresponding tissue temperature or tissue pressure;

estimating, using the at least one machine learning algorithm, a tissue parameter based on the at least one observed electrical parameter, wherein the estimated tissue parameter includes an estimated tissue temperature and an estimated tissue pressure;

communicate the estimated tissue parameter to a computing device associated with the energy source for use in formulating an energy-delivery algorithm for delivering energy from the instrument to tissue; and delivering energy from the instrument of the surgical system to tissue in accordance with the energy-delivery algorithm.

12. The system of claim 11, wherein collecting the data from the surgical system includes measuring at least one of a voltage, a current, or a frequency.

13. The system of claim 11, wherein the at least one machine learning algorithm includes a neural network.

14. The system of claim 13, wherein the neural network includes at least one of a temporal convolutional network or a feed forward network.

15. The system of claim 13, wherein:

communicating the data to at least one machine learning algorithm includes:

shifting data into the machine learning algorithm one time step at a time; and estimating the tissue parameter includes estimating, by the machine learning algorithm, the tissue parameter one time step at a time.

16. The system of claim 13, wherein the instructions, when executed by the one or more processors, further cause the system to train the neural network using one or more of observing sensor data or identifying patterns in data.

17. The system of claim 13, wherein the instructions, when executed by the one or more processors, further cause the system to train the neural network using training data including at least one of: impedance, power, time, tissue electrical properties, tissue thermal properties, electrical properties of the instrument, thermal properties of the instrument, size of the instrument, shape of the instrument, frequency, voltage, current, balun temperature, or transformer temperature.

18. The system of claim 13, wherein the estimating includes estimating tissue temperature without a temperature sensor.

19. The system of claim 13, wherein the energy source is adapted to generate energy for treating tissue, the energy source including one or more output terminals which supply energy to the tissue, the one or more output terminals operatively connected to one or more supply lines, the energy source including one or more return terminals configured to return energy from the tissue, the return terminals being operatively connected to one or more return lines,
- wherein the surgical system further includes a cable housing a portion of the one or more supply lines and the one or more return lines; and
- wherein the instrument is operatively connected to the cable.

20. The system of claim 13, wherein the surgical system includes at least one of a microwave ablation system, an electrosurgical system, or an ultrasonic surgical instrument.

* * * * *